(12) United States Patent
Kim et al.

(10) Patent No.: US 8,410,302 B2
(45) Date of Patent: Apr. 2, 2013

(54) METHOXYIMINO COMPOUNDS AND FUNGICIDE COMPOSITION COMPRISING SAME

(75) Inventors: Joo-Kyung Kim, Gyeongju-si (KR); Hyung-Ho Kim, Daejeon (KR); In-Cheon Hwang, Gyeongju-si (KR); Ho-tae Nam, Daegu (KR)

(73) Assignee: Kyung Nong Corporation, Seoul (KR)

( * ) Notice: Subject to any disclaimer, the term of this patent is extended or adjusted under 35 U.S.C. 154(b) by 327 days.

(21) Appl. No.: 12/746,469

(22) PCT Filed: Dec. 5, 2008

(86) PCT No.: PCT/KR2008/007205
§ 371 (c)(1),
(2), (4) Date: Aug. 11, 2010

(87) PCT Pub. No.: WO2009/072837
PCT Pub. Date: Jun. 11, 2009

(65) Prior Publication Data
US 2010/0298593 A1      Nov. 25, 2010

(30) Foreign Application Priority Data

Dec. 6, 2007 (KR) .................. 10-2007-0125883
Aug. 13, 2008 (KR) .................. 10-2008-0079429

(51) Int. Cl.
*C07C 229/00* (2006.01)
*A01N 35/10* (2006.01)
*A01N 47/40* (2006.01)

(52) U.S. Cl. ........................................ 560/35; 504/343

(58) Field of Classification Search ........................ None
See application file for complete search history.

(56) References Cited

FOREIGN PATENT DOCUMENTS

| | | |
|---|---|---|
| EP | 0 398 692 A2 | 11/1990 |
| EP | 0 585 751 A1 | 3/1994 |
| EP | 0 811 608 A1 | 12/1997 |
| JP | 2002-520383 A | 7/2002 |
| JP | 2006-199765 A | 8/2006 |
| WO | 00/03974 A | 1/2000 |

OTHER PUBLICATIONS

European Patent Office, European Search Report issued in corresponding EP Application No. 08857852.1, dated Mar. 2, 2012.
Takenaka et al., Structure and Fungicidal Activities of 2-methoxyimino-N-methyl-2-[2-(substituted pyridyloxymetyyl)phenyl]acetamide Derivative, J. Pesticide Sci. 23, 379-85 (1998).
Takenaka et al., "Fungicidal Activities of 2-(Substituted Phenoxymethyl)phenyl-2-methoxyiminoacetamide Derivatives," J. Pesticide Sci., 1998, vol. 23, pp. 107-112.
Japanese Patent Office, Japanese Office Action issued in corresponding JP Application No. 2010-536853, dated Nov. 27, 2012.
Tanaka et al., "Reductive Addition of Polyhalomethanes and their Related Compounds to Aldehydes and 1,2-elimination of the Coupling Products in a Palladium/Aluminum Bimetal Redox System," Journal of Organic Chemistry, 1989, vol. 54, No. 2, pp. 444-450.

*Primary Examiner* — Susanna Moore
*Assistant Examiner* — Jennifer C Sawyer
(74) *Attorney, Agent, or Firm* — Sughrue Mion, PLLC

(57) ABSTRACT

The present invention provides a methoxyimino compound, and a fungicide composition comprising same as an active ingredient. The methoxyimino compound of the present invention, which has an excellent antifungal activity against a wide spectrum of fungi even at a low application rate, can be used to protect various crops.

10 Claims, No Drawings

METHOXYIMINO COMPOUNDS AND FUNGICIDE COMPOSITION COMPRISING SAME

CROSS REFERENCE TO RELATED APPLICATIONS

This application is a National Stage of International Application No. PCT/KR2008/007205 filed Dec. 5, 2008, claiming priority based on Korean Patent Application Nos. 10-2007-0125883, filed Dec. 6, 2007, and 10-2008-0079429, filed Aug. 13, 2008, the contents of all of which are incorporated herein by reference in their entirety.

FIELD OF THE INVENTION

The present invention relates to a novel methoxyimino compound, and a fungicide composition comprising same.

BACKGROUND OF THE INVENTION

Highly active natural antifungal materials such as strobilurin A, B and C as well as oudemansin A and B have a common structural feature of comprising a β-methoxyacrylate (MOA) framework, which has stimulated studies to develop methoxyimino ester or amide fungicide having the same framework.

Such methoxyimino esters or amides compounds have excellent antifungal activity at a low dosage rate, good penetration and translocation proportion, and a broad range of antifungal applicability. These characteristics solve the problems of the existing drugs such as low activity, a narrow antifungal range and short activity durability. However, the repetitive use thereof induces the appearance of new fungal strains resistant not only to said fungicides but also to related fungicides having a common structural feature.

For this reason, continuous efforts have been undertaken to develop novel fungicides. Such efforts have led to the development of new fungicides derived from strobilurin disclosed in, for example, International Patent Publication Nos. WO 96/06072, WO 96/33164, WO 98/56774 and WO 99/23066, German Patent Nos. 724,200 (1997) and 732,846 (1997), and Great Britain Patent No. 22,893 (1997). However, these compounds still suffer from the problem of a narrow antifungal spectrum or low activity against different fungi such as *Phytophthora*.

Therefore, the present inventors have endeavored to develop a highly effective compound having stronger antifungal activity, a much broader range of antifungal applicability, a lower toxicity, and improved activity durability than existing fungicides, and developed a compound having excellent antifungal activity for protecting crops from fungal damages even at a low application rate.

SUMMARY OF THE INVENTION

Accordingly, it is an object of the present invention to provide an antifungal methoxyimino compound having excellent antifungal activity against a wide spectrum of fungi even at a low application rate to protect various crops, and a method for preparing same.

It is another object of the present invention to provide a fungicide composition comprising the methoxyimino compound as an active ingredient.

In accordance with one aspect of the present invention, there is provided a methoxyimino compound of formula (I):

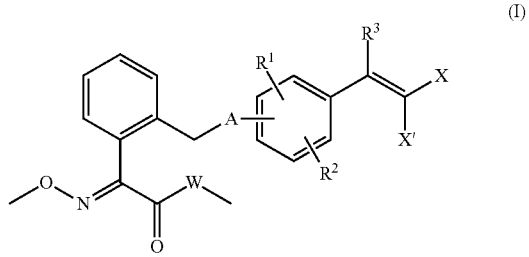

wherein,
A is O or O—N=C(CH$_3$);
R$^1$ is H, halogen, C$_{1-3}$ alkyl, or C$_{1-3}$ alkoxy;
R$^2$ is H or C$_{1-3}$ alkoxy;
R$^3$ is H, or C$_{1-4}$ alkyl substituted with one or more C$_{1-4}$ alkyl groups or halogens;
X and X' are each independently halogen; and
W is O or NH.

In accordance with another aspect of the present invention, there is provided a method for preparing the methoxyimino compound of formula (I).

In accordance with further another aspect of the present invention, there is provided a fungicide composition comprising the methoxyimino compound of formula (I) as an active ingredient.

DETAILED DESCRIPTION OF THE INVENTION

The methoxyimino compound of formula (I) according to the present invention is a novel compound introduced with a styrene substituent having two or more halogen atoms.

In the inventive methoxyimino compound of formula (I), preferably, X and X' are each independently F, Cl or Br; R$^1$ is H, F, Cl, Br, methyl, methoxy or ethoxy; R$^2$ is H or methoxy; and R$^3$ is H, or C$_{1-4}$ alkyl substituted with one or more fluorines.

The more preferred methoxyimino compounds of formula (I) according to the present invention are the following examples:
(1) methyl-(E)-2-(2-((3-(2,2-dichlorovinyl)phenoxy)methyl)phenyl)-2-methoxyimino acetate;
(2) (E)-2-(2-((3-(2,2-dichlorovinyl)phenoxy)methyl)phenyl)-2-methoxyimino-N-methylacetamide;
(3) methyl-(E)-2-(2-((4-(2,2-dichlorovinyl)phenoxy)methyl)phenyl)-2-methoxyiminoacetate;
(4) (E)-2-(2-((4-(2,2-dichlorovinyl)phenoxy)methyl)phenyl)-2-methoxyimino-N-methylacetamide;
(5) methyl-(E)-2-(2-((3-(2,2-dibromovinyl)phenoxy)methyl)phenyl)-2-methoxyiminoacetate;
(6) (E)-2-(2-((3-(2,2-dibromovinyl)phenoxy)methyl)phenyl)-2-methoxyimino-N-methylacetamide;
(7) methyl-(E)-2-(2-((4-(2,2-dibromovinyl)phenoxy)methyl)phenyl)-2-methoxyiminoacetate;
(8) (E)-2-(2-((4-(2,2-dibromovinyl)phenoxy)methyl)phenyl)-2-methoxyimino-N-methylacetamide;
(9) methyl-(E)-2-(2-((4-(2,2-difluorovinyl)phenoxy)methyl)phenyl)-2-methoxyiminoacetate;
(10) (E)-2-(2-((4-(2,2-difluorovinyl)phenoxy)methyl)phenyl)-2-methoxyimino-N-methylacetamide;
(11) methyl-(2E)-2-(2-((3-(2-chloro-2-fluorovinyl)phenoxy)methyl)phenyl)-2-methoxyiminoacetate;

(12) (2E)-2-(2-((3-(2-chloro-2-difluorovinyl)phenoxy)methyl)phenyl)-2-methoxyimino-N-methylacetamide;
(13) methyl-(2E)-2-(2-((4-(2-chloro-2-fluorovinyl)phenoxy)methyl)phenyl)-2-methoxyiminoacetate;
(14) (2E)-2-(2-((4-(2-chloro-2-difluorovinyl)phenoxy)methyl)phenyl)-2-methoxyimino-N-methylacetamide;
(15) methyl-(2E)-2-(2-((3-(2-bromo-2-chlorovinyl)phenoxy)methyl)phenyl)-2-methoxyiminoacetate;
(16) (2E)-2-(2-((3-(2-bromo-2-chlorovinyl)phenoxy)methyl)phenyl)-2-methoxyimino-N-methylacetamide;
(17) methyl-(2E)-2-(2-((4-(2-bromo-2-chlorovinyl)phenoxy)methyl)phenyl)-2-methoxyiminoacetate;
(18) (2E)-2-(2-((4-(2-bromo-2-chlorovinyl)phenoxy)methyl)phenyl)-2-methoxyimino-N-methylacetamide;
(19) methyl-(E)-2-[[[[[2-[3-(2,2-dichlorovinyl)phenyl](1-methyl)methylidene]amino]oxy]methyl]phenyl]-2-methoxyiminoacetate;
(20) (E)-2-[[[[[2-[3-(2,2-dichlorovinyl)phenyl](1-methyl)methylidene]amino]oxy]methyl]phenyl]-2-methoxyimino-N-methylacetamide;
(21) methyl-(E)-2-[[[[[2-[4-(2,2-dichlorovinyl)phenyl](1-methyl)methylidene]amino]oxy]methyl]phenyl]-2-methoxyiminoacetate;
(22) (E)-2-[[[[[2-[4-(2,2-dichlorovinyl)phenyl](1-methyl)methylidene]amino]oxy]methyl]phenyl]-2-methoxyimino-N-methylacetamide;
(23) methyl-(E)-2-[[[[[2-[3-(2,2-dibromovinyl)phenyl](1-methyl)methylidene]amino]oxy]methyl]phenyl]-2-methoxyiminoacetate;
(24) (E)-2-[[[[[2-[3-(2,2-dibromovinyl)phenyl](1-methyl)methylidene]amino]oxy]methyl]phenyl]-2-methoxyimino-N-methylacetamide;
(25) methyl-(E)-2-[[[[[2-[4-(2,2-dibromovinyl)phenyl](1-methyl)methylidene]amino]oxy]methyl]phenyl]-2-methoxyiminoacetate;
(26) (E)-2-[[[[[2-[4-(2,2-dibromovinyl)phenyl](1-methyl)methylidene]amino]oxy]methyl]phenyl]-2-methoxyimino-N-methylacetamide;
(27) methyl-(E)-2-[[[[[2-[3-(2,2-difluorovinyl)phenyl](1-methyl)methylidene]amino]oxy]methyl]phenyl]-2-methoxyiminoacetate;
(28) (E)-2-[[[[[2-[3-(2,2-difluorovinyl)phenyl](1-methyl)methylidene]amino]oxy]methyl]phenyl]-2-methoxyimino-N-methylacetamide;
(29) methyl-(E)-2-[[[[[2-[4-(2,2-difluorovinyl)phenyl](1-methyl)methylidene]amino]oxy]methyl]phenyl]-2-methoxyiminoacetate;
(30) (E)-2-[[[[[2-[4-(2,2-difluorovinyl)phenyl](1-methyl)methylidene]amino]oxy]methyl]phenyl]-2-methoxyimino-N-methylacetamide;
(31) methyl-(E)-2-[[[[[2-[3-(2-chloro-2-fluorovinyl)phenyl](1-methyl)methylidene]amino]oxy]methyl]phenyl]-2-methoxyiminoacetate;
(32) (E)-2-[[[[[2-[3-(2-chloro-2-fluorovinyl)phenyl](1-methyl)methylidene]amino]oxy]methyl]phenyl]-2-methoxyimino-N-methylacetamide;
(33) methyl-(E)-2-[[[[[2-[4-(2-chloro-2-fluorovinyl)phenyl](1-methyl)methylidene]amino]oxy]methyl]phenyl]-2-methoxyiminoacetate;
(34) (E)-2-[[[[[2-[4-(2-chloro-2-fluorovinyl)phenyl](1-methyl)methylidene]amino]oxy]methyl]phenyl]-2-methoxyimino-N-methylacetamide;
(35) methyl-(E)-2-[[[[[2-[3-(2-bromo-2-chlorovinyl)phenyl](1-methyl)methylidene]amino]oxy]methyl]phenyl]-2-methoxyiminoacetate;
(36) (E)-2-[[[[[2-[3-(2-bromo-2-chlorovinyl)phenyl](1-methyl)methylidene]amino]oxy]methyl]phenyl]-2-methoxyimino-N-methylacetamide;
(37) methyl-(E)-2-[[[[[2-[4-(2-bromo-2-chlorovinyl)phenyl](1-methyl)methylidene]amino]oxy]methyl]phenyl]-2-methoxyiminoacetate;
(38) (E)-2-[[[[[2-[4-(2-bromo-2-chlorovinyl)phenyl](1-methyl)methylidene]amino]oxy]methyl]phenyl]-2-methoxyimino-N-methylacetamide;
(39) methyl-(E)-2-(2-((2-chloro-4-(2,2-dichlorovinyl)phenoxy)methyl)phenyl)-2-methoxyiminoacetate;
(40) (E)-2-(2-((2-chloro-4-(2,2-dichlorovinyl)phenoxy)methyl)phenyl)-2-methoxyimino-N-methylacetamide;
(41) methyl-(E)-2-(2-((4-(2,2-dichlorovinyl)-2-methylphenoxy)methyl)phenyl)-2-methoxyiminoacetate;
(42) (E)-2-(2-((4-(2,2-dichlorovinyl)-2-methylphenoxy)methyl)phenyl)-2-methoxyimino-N-methylacetamide;
(43) methyl-(E)-2-(2-((2-chloro-3-(2,2-dichlorovinyl)phenoxy)methyl)phenyl)-2-methoxyiminoacetate;
(44) (E)-2-(2-((2-chloro-3-(2,2-dichlorovinyl)phenoxy)methyl)phenyl)-2-methoxyimino-N-methylacetamide;
(45) methyl-(E)-2-(2-((2-(2,2-dichlorovinyl)-4-methylphenoxy)methyl)phenyl)-2-methoxyiminoacetate;
(46) (E)-2-(2-((2-(2,2-dichlorovinyl)-4-methylphenoxy)methyl)phenyl)-2-methoxyimino-N-methylacetamide;
(47) methyl-(E)-2-(2-((5-(2,2-dichlorovinyl)-2-methoxyphenoxy)methyl)phenyl)-2-methoxyiminoacetate;
(48) (E)-2-(2-((5-(2,2-dichlorovinyl)-2-methoxyphenoxy)methyl)phenyl)-2-methoxyimino-N-methylacetamide;
(49) methyl-(E)-2-(2-((2-(2,2-dichlorovinyl)-6-methylphenoxy)methyl)phenyl)-2-methoxyiminoacetate;
(50) (E)-2-(2-((2-(2,2-dichlorovinyl)-6-methylphenoxy)methyl)phenyl)-2-methoxyimino-N-methylacetamide;
(51) methyl-(E)-2-(2-((2-bromo-3-(2,2-dichlorovinyl)-6-methoxyphenoxy)methyl)phenyl)-2-methoxyiminoacetate;
(52) (E)-2-(2-((2-(2-bromo-3-(2,2-dichlorovinyl)-6-phenoxy)methyl)phenyl)-2-methoxyimino-N-methylacetamide;
(53) methyl-(E)-2-(2-((2-bromo-4-(2,2-dichlorovinyl)phenoxy)methyl)phenyl)-2-methoxyiminoacetate;
(54) (E)-2-(2-((2-bromo-4-(2,2-dichlorovinyl)phenoxy)methyl)phenyl)-2-methoxyimino-N-methylacetamide;
(55) methyl-(E)-2-(2-((2-(2,2-dichlorovinyl)-4-fluorophenoxy)methyl)phenyl)-2-methoxyiminoacetate;
(56) (E)-2-(2-((2-(2,2-dichlorovinyl)-4-fluorophenoxy)methyl)phenyl)-2-methoxyimino-N-methylacetamide;
(57) methyl-(E)-2-(2-((3-chloro-4-(2,2-dichlorovinyl)phenoxy)methyl)phenyl)-2-methoxyiminoacetate;
(58) (E)-2-(2-((3-chloro-4-(2,2-dichlorovinyl)phenoxy)methyl)phenyl)-2-methoxyimino-N-methylacetamide;
(59) methyl-(E)-2-(2-((4-(2,2-dichlorovinyl)-2-ethoxyphenoxy)methyl)phenyl)-2-methoxyiminoacetate;
(60) (E)-2-(2-((4-(2,2-dichlorovinyl)-2-ethoxyphenoxy)methyl)phenyl)-2-methoxyimino-N-methylacetamide;
(61) methyl-(E)-2-(2-((5-bromo-2-(2,2-dichlorovinyl)phenoxy)methyl)phenyl)-2-methoxyiminoacetate;
(62) (E)-2-(2-((5-bromo-2-(2,2-dichlorovinyl)phenoxy)methyl)phenyl)-2-methoxyimino-N-methylacetamide;
(63) methyl-(E)-2-(2-((4-(2,2-dibromovinyl)-2-chlorophenoxy)methyl)phenyl)-2-methoxyiminoacetate;
(64) (E)-2-(2-((4-(2,2-dibromovinyl)-2-chlorophenoxy)methyl)phenyl)-2-methoxyimino-N-methylacetamide;
(65) methyl-(E)-2-(2-((4-(2,2-dibromovinyl)-2-methylphenoxy)methyl)phenyl)-2-methoxyiminoacetate;
(66) (E)-2-(2-((4-(2,2-dibromovinyl)-2-methylphenoxy)methyl)phenyl)-2-methoxyimino-N-methylacetamide;

(67) methyl-(E)-2-(2-((3-(2,2-dibromovinyl)-2-chlorophenoxy)methyl)phenyl)-2-methoxyiminoacetate;
(68) (E)-2-(2-((3-(2,2-dibromovinyl)-2-chlorophenoxy)methyl)phenyl)-2-methoxyimino-N-methylacetamide;
(69) methyl-(E)-2-(2-((2-(2,2-dibromovinyl)-4-methylphenoxy)methyl)phenyl)-2-methoxyiminoacetate;
(70) (E)-2-(2-((2-(2,2-dibromovinyl)-4-methylphenoxy)methyl)phenyl)-2-methoxyimino-N-methylacetamide;
(71) methyl-(E)-2-(2-((5-(2,2-dibromovinyl)-2-methoxyphenoxy)methyl)phenyl)-2-methoxyiminoacetate;
(72) (E)-2-(2-((5-(2,2-dibromovinyl)-2-methoxyphenoxy)methyl)phenyl)-2-methoxyimino-N-methylacetamide;
(73) methyl-(E)-2-(2-((2-(2,2-dibromovinyl)-6-methylphenoxy)methyl)phenyl)-2-methoxyiminoacetate;
(74) (E)-2-(2-((2-(2,2-dibromovinyl)-6-methylphenoxy)methyl)phenyl)-2-methoxyimino-N-methylacetamide;
(75) methyl-(E)-2-(2-((2-bromo-3-(2,2-dibromovinyl)-6-methoxyphenoxy)methyl)phenyl)-2-methoxyiminoacetate;
(76) (E)-2-(2-((2-(2-bromo-3-(2,2-dibromovinyl)-6-methoxyphenoxy)methyl)phenyl)-2-methoxyimino-N-methylacetamide;
(77) methyl-(E)-2-(2-((2-bromo-4-(2,2-dibromovinyl)phenoxy)methyl)phenyl)-2-methoxyiminoacetate;
(78) (E)-2-(2-((2-bromo-4-(2,2-dibromovinyl)phenoxy)methyl)phenyl)-2-methoxyimino-N-methylacetamide;
(79) methyl-(E)-2-(2-((2-(2,2-dibromovinyl)-4-fluorophenoxy)methyl)phenyl)-2-methoxyiminoacetate;
(80) (E)-2-(2-((2-(2,2-dibromovinyl)-4-fluorophenoxy)methyl)phenyl)-2-methoxyimino-N-methylacetamide;
(81) methyl-(E)-2-(2-((4-(2,2-dibromovinyl)-3-chlorophenoxy)methyl)phenyl)-2-methoxyiminoacetate;
(82) (E)-2-(2-((4-(2,2-dibromovinyl)-3-chlorophenoxy)methyl)phenyl)-2-methoxyimino-N-methylacetamide;
(83) methyl-(E)-2-(2-((4-(2,2-dibromovinyl)-2-ethoxyphenoxy)methyl)phenyl)-2-methoxyiminoacetate;
(84) (E)-2-(2-((4-(2,2-dibromovinyl)-2-ethoxyphenoxy)methyl)phenyl)-2-methoxyimino-N-methylacetamide;
(85) methyl-(E)-2-(2-((5-bromo-2-(2,2-dibromovinyl)phenoxy)methyl)phenyl)-2-methoxyiminoacetate; and
(86) (E)-2-(2-((5-bromo-2-(2,2-dibromovinyl)phenoxy)methyl)phenyl)-2-methoxyimino-N-methylacetamide.

A methoxyimino ester compound of formula (Ia), which corresponds to the compound of formula (I) wherein W is O, may be prepared, for example, by subjecting the bromide of formula (II) to a substitution reaction with the dihalostyrene compound of formula (III) in the presence of a base.

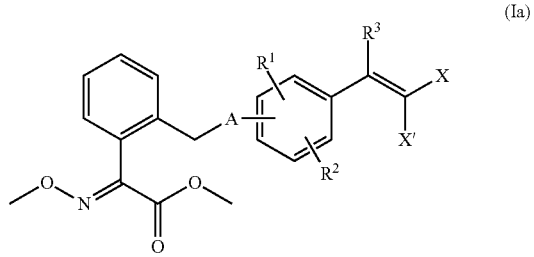

(Ia)

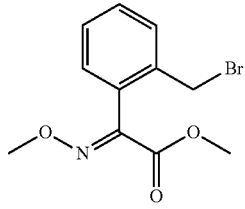

(II)

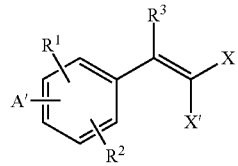

(III)

wherein,
A' is OH or C(CH$_3$)=NOH,
A, X, X', R$^1$, R$^2$ and R$^3$ have the same meanings as defined in formula (I).

The base used in the method for preparing the compound of formula (Ia) of the present invention may be triethylamine, potassium carbonate or sodium hydroxide, and the base is preferably diluted in an organic solvent such as toluene, hexane, xylene, ethyl acetate, acetonitrile, dichloroethane, methylene chloride or tetrahydrofuran.

In the present invention, the reaction may be carried out at a temperature ranging from −10° C. to 150° C. When the reaction is completed, the solid formed is removed by filtration, the organic solvent is removed by evaporating, and the resulting residue is isolated by chromatography to obtain the compound of formula (Ia).

In the present invention, the compound of formula (III) may be used in an amount of 0.5 to 1 mole, preferably 0.9 to 1 mole based on 1 mole of the compound of formula (II).

In the present invention, the compounds of formula (II) and (III) used as a starting materials are commercially available or they may be prepared according to the conventional methods.

When the compound of formula (II) is prepared, for example, as shown in Reaction Scheme (A), methyl-(2E)-2-methoxyimino-2-(2'-bromomethyl)phenylacetate may be synthesized from 2-methylbenzoyl chloride by nitrilization, oxalation, condensation and bromination reaction (see, [Rambaud, M. et al., *Synthesis,* 564 (1988)]; Korean Patent Publication Nos. 98-83587 and 99-15785; and International Patent Publication No. WO 99/07665):

Reaction Scheme (A)

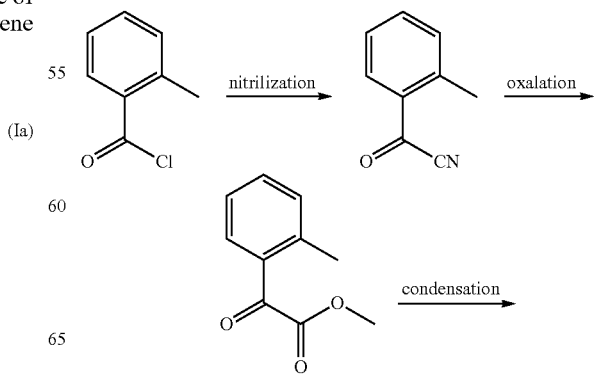

-continued

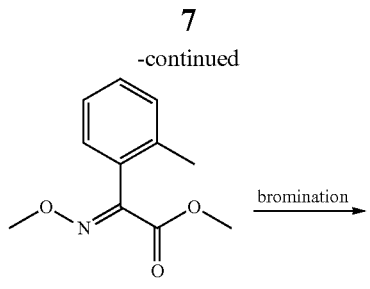

bromination →

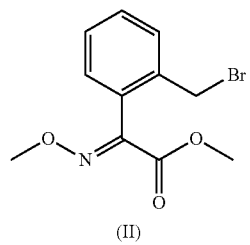
(II)

Further, the dihalostyrene compound of formula (III) may be the compound of formula (IIIa) or (IIIb):

(IIIa)

(IIIb)

wherein, X, X', $R^1$, $R^2$ and $R^3$ have the same meanings as defined in formula (I).

Specifically, the compound of formula (IIIa) may be prepared by a conventional method, for example, as shown in Reaction Scheme (B), by haloalkenylation of 2-, 3- or 4-hydroxybenzaldehyde (see [Valentine, G et al., *Eur. J. Org. Chem.*, 302 (2003)]; [Vasily, N et al., *Tetrahedron* Vol. 57, 7519 (2001)]; [Alexey, V et al., *Tetrahedron* Vol. 56, 6557 (2000)]; [Hideo, T et al., *J. Org. Chem.*, Vol. 54, 444 (1989)]; and [Jian, L et al., *Tetrahedron Lett.*, Vol. 44, 9349 (2003)]):

Reaction Scheme (B)

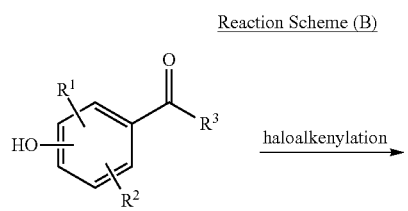

haloalkenylation →

-continued (IIIa)

wherein, X, X', $R^1$, $R^2$ and $R^3$ have the same meanings as defined in formula (I).

The compound of formula (IIIb) may be prepared as shown in Reaction Scheme (C), by haloalkenylation of 2-, 3- or 4-acetylbenzaldehyde and condensation (see [*Tetrahedron Lett.*, 3251 (2000)]; [Vasily, N et al., *Tetrahedron* Vol. 57, 7519 (2001)]; and [Hideo, T et al., *J. Org. Chem.*, Vol. 54, 444 (1989)]):

Reaction Scheme (C)

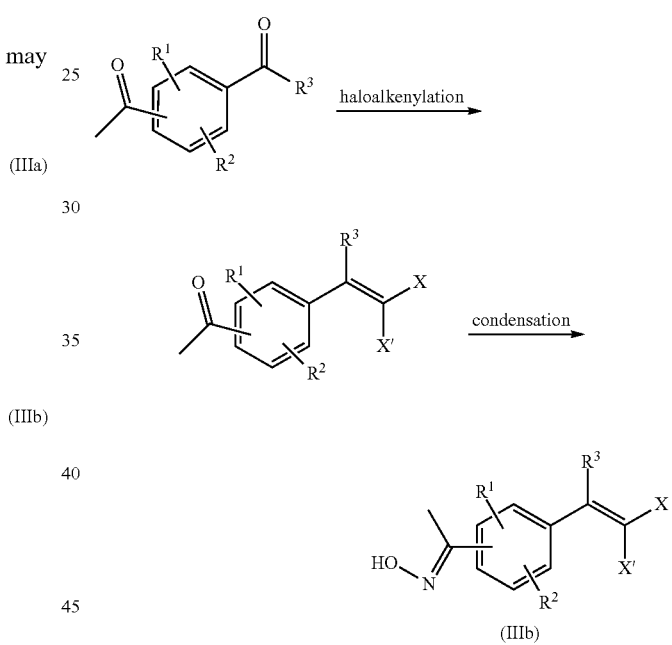

(IIIb)

wherein, X, X', $R^1$, $R^2$ and $R^3$ have the same meanings as defined in formula (I).

Further, the methoxyimino ester compound of formula (Ia) of the present invention may be prepared by subjecting the compound of formula (IV) to a substitution reaction with a halogenated compound having 2 or more halogen atoms.

(Ia)

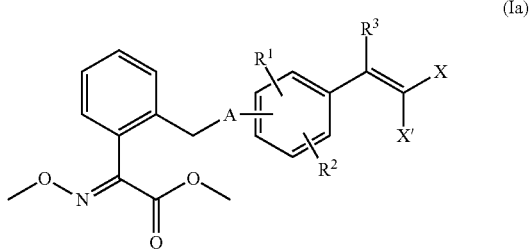

-continued

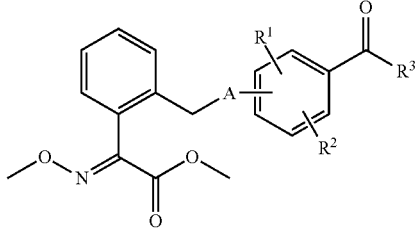

(IV)

wherein, A, X, X', R¹, R² and R³ have the same meanings as defined in formula (I).

The halogenated compound used in the above reaction is preferably chloroform, $CCl_4$, $CBr_4$, $CF_2Br_2$, $CFCl_3$, or CClBr, and it is used in an amount of 1 to 6 moles, preferably 2 to 4 moles based on 1 mole of the compound of formula (IV).

The substitution may be carried out at a temperature ranging from 0 to 100° C., preferably from 10 to 50° C. The reaction may be performed in a solvent such as ethyl acetate, toluene, acetonitrile, xylene, hexane, methylene chloride, dimethylformamide, dichloroethane or tetrahydrofuran, in the presence of a metal catalyst such as a combination of aluminum and lead bromide. After the reaction is completed, the solid was removed by filteration, the organic solvent was evaporated, and the resulting residue was isolated and purified by chromatography to obtain the compound of formula (Ia) of the present invention.

The compound of formula (IV) may be prepared, as shown in Reaction Scheme (D), by a substitution reaction of 2-, 3- or 4-hydroxybenzaldehyde with the compound of formula (II):

Reaction Scheme (D)

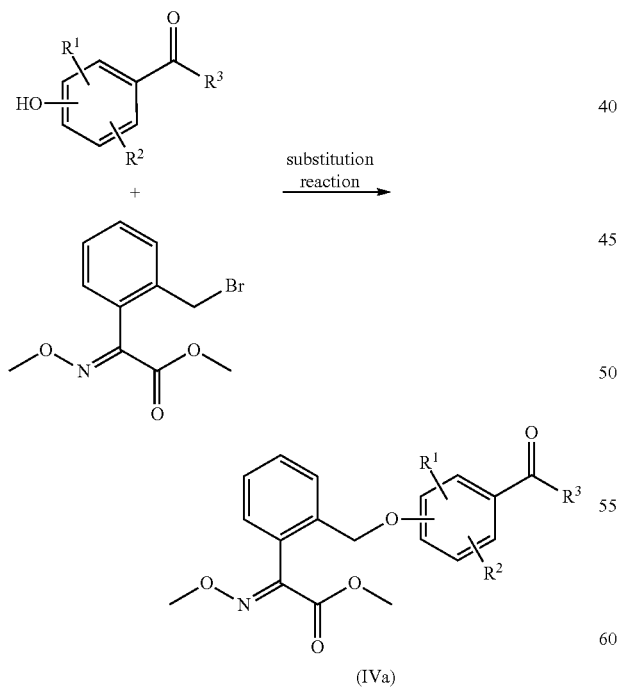

(IVa)

wherein, R¹, R² and R³ have the same meanings as defined in formula (I).

The compound of formula (IV) may also be prepared as shown in Reaction Scheme (E) from 2-, 3- or 4-acetylbenzaldehyde through condensation and substitution reactions (see [*Tetrahedron Lett.*, 3251 (2000)]; [Vasily, N et al., *Tetrahedron* Vol. 57, 7519 (2001)]; and [Hideo, T et al., *J. Org. Chem.*, Vol. 54, 444 (1989)]):

Reaction Scheme (E)

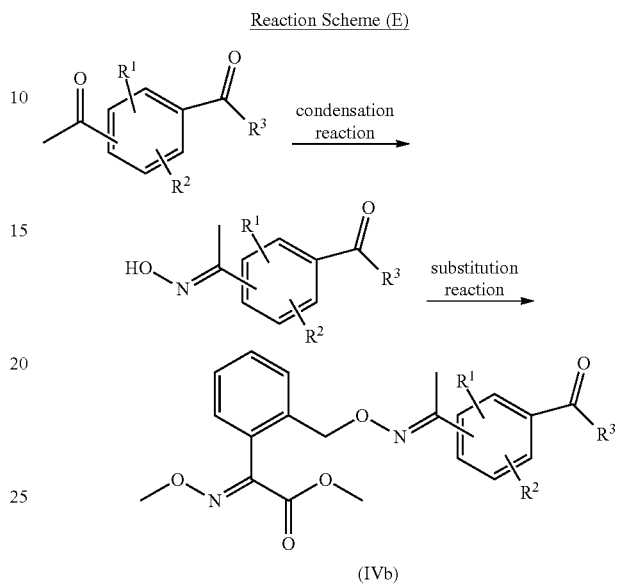

(IVb)

wherein, R¹, R² and R³ have the same meanings as defined in formula (I).

The methoxy amide compound of formula (Ib), which is the compound of formula (I) according to the present invention wherein W is NH, may be prepared by subjecting the compound of formula (Ia) to amidation.

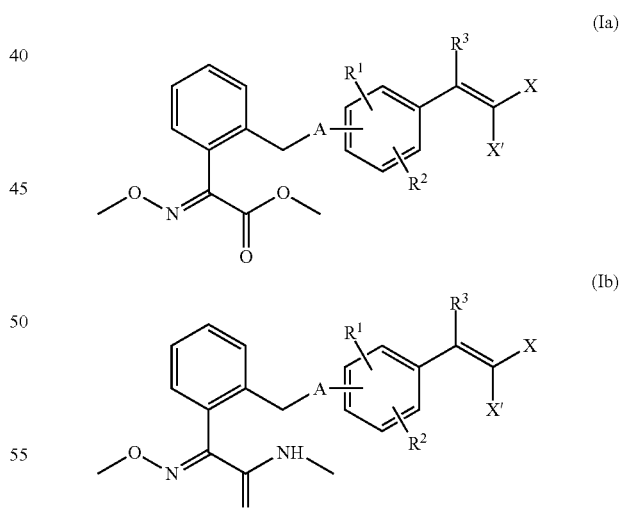

wherein, A, X, X', R¹, R² and R³ have the same meanings as defined in formula (I).

Specifically, the amide compound of formula (Ib) may be prepared by dissolving the compound of formula (Ia) in methanol, adding 40% aqueous methylamine thereto, and stirring for 6 hours at −10° C. to room temperature.

The compound of formula (I) of the present invention prepared in accordance with the above method has an excellent fungicidal activity. Therefore, the present invention provides a fungicide composition comprising thereof as an active ingredient.

The composition according to the present invention may be formulated in various forms by mixing at least one of the compound of formula (I) with an appropriate additive (e.g.: carrier or diluent) such as an emulsion, wettable powder, suspension concentrate, powder and granules. For example, the active ingredient may be used in an amount of 1 to 50% based on the weight of an emulsion wettable powder or suspension concentrate, 0.1 to 50% based on the weight of a powder, and 0.1 to 20% based on the weight of a granule, but not limited thereto.

The carrier that may be used in the composition of the present invention may be a liquid carrier and a solid carrier. The liquid carrier may include water, alcohols (e.g.: primary alcohol such as methanol, secondary alcohol such as ethylene glycol or tertiary alcohol such as glycerin), ketones (e.g.: acetone or methylethylketone), ethers (e.g.: dioxane, tetrahydrofuran (THF) or cellosolve), aliphatic hydrocarbons (e.g.: gasoline or kerosene), halogenated hydrocarbons (e.g.: chloroform or carbon tetrachloride), acid amides (e.g.: dimethylformamide), esters (e.g.: ethyl acetate, butyl acetate or aliphatic glycerin ester) and acetonitrile, and in the present invention, the carrier may be used solely or in a mixture thereof. Further, the solid carrier may include a mineral particle (e.g.: kaolin, clay, bentonite, acid clay, talc, silica or sand). Further, the inventive composition may further comprise an emulsifier, adhesive, dispersing agent or wetting agent, for example, a nonionic, anionic or cationic surfactant such as fatty acid soda polyoxy alkylesters, alkyl sulfonates or polyethyleneglycolesters.

Further, an agrochemically active ingredient, e.g., an insecticide, herbicide, plant growth regulator, germicide, and fertilizer, may be added in the composition of the present invention.

The following Examples are intended to further illustrate the present invention without limiting its scope.

Example

Preparation Example 1

Preparation of methyl-(2E)-2-methoxyimino-2-(2'-bromomethyl)phenylacetate (Compound of Formula (II))

Step 1) Preparation of 2-oxo-O-tolylacetonitrile

2-Methylbenzoylchloride (30.9 g, 0.2 mol) and sodium cyanide (10.8 g, 0.22 mol) were dissolved in 200 ml of dichloromethane, the mixture was stirred at room temperature for 2 hours and extracted with dichloroethane. The organic layer was washed 2-3 times with water, dried over magnesium sulfate, filtered and distilled. The resulting residue was subjected to silica gel column chromatography (ethyl acetate:n-hexane=1:4) to obtain the title compound as a colorless liquid (26.71 g, 92%).
$^1$H-NMR (CDCl$_3$, TMS) d (ppm): 7.88-7.01 (m, 4H), 2.35 (s, 3H)

Step 2) Preparation of methyl 2-oxo-2-O-tolylacetate 12 ml of 85% sulfuric acid was slowly added to a mixture of 2-oxo-O-tolylacetonitrile (14.5 g, 0.1 mol) obtained in Step 1 and sodium bromide (0.52 g, 1 mmol) thereto, and the mixture was stirred for 1 hour. 15 ml of methanol was slowly added to the reaction mixture, and the mixture was refluxed for 2 hours. The solvent was removed therefrom under a reduced pressure, and the filtrate was extracted three times with dichloroethane. The organic layer was washed 2-3 times with water, dried over magnesium sulfate, filtered and distilled. The resulting residue was subjected to silica gel column chromatography (ethyl acetate:n-hexane=1:4) to obtain the title compound as a colorless liquid (14.8 g, 83%).
$^1$H-NMR (CDCl$_3$, TMS) d (ppm): 7.88-7.01 (m, 4H), 3.67 (s, 3H), 2.35 (s, 3H)

Step 3) Preparation of methyl-(2E)-2-methoxyimino-2-(2'-methyl)phenylacetate

O-methylhydroxylamine hydrochloride (8.35 g, 0.1 mol) and pyridine (8.1 ml, 0.1 mol) were mixed to methanol (100 ml), methyl 2-oxo-2-O-tolylacetate (17.8 g, 0.1 mol) obtained in Step 2 was added thereto, and the mixture was stirred and heated for 12 hours. After drying the reaction mixture under a reduced pressure, water was added thereto, and the mixture was extracted with ethyl acetate. The organic layer was dried over magnesium sulfate, filtered and distilled. The resulting residue was subjected to silica gel column chromatography (ethyl acetate:n-hexane=1:4) to obtain the title compound as a colorless liquid (19.07 g, 92%).

The title compound thus obtained had two isomers, and was composed of 25% liquid product (upper spot) and 75% solid product (down spot) at a ratio of 1:3. These isomers were separated, and the solid product was recrystallized with n-hexane. The product thus obtained having m.p. of 63 to 64° C. was subjected to X-ray crystallography, and it was confirmed that the product was the E isomer. The E isomer was used in the following step.

Z isomer (upper spot): colorless liquid compound
$^1$H-NMR (CDCl$_3$, TMS) d (ppm): 7.41-7.15 (m, 4H), 4.01 (s, 3H), 3.85 (s, 3H), 2.45 (s, 3H)

E isomer (down spot): colorless solid compound
$^1$H-NMR (CDCl$_3$, TMS) d (ppm): 7.38-7.05 (m, 4H), 4.04 (s, 3H), 3.85 (s, 3H), 2.19 (s, 3H)

Step 4) Preparation of methyl-(2E)-2-methoxyimino-2-(2'-bromomethyl)phenylacetate Methyl-(2E)-2-methoxyimino-2-(2'-methyl)phenylacetate (9.0 g, 0.0435 mol) obtained in Step 3 and N-bromosuccinimide (NBS, 7.74 g, 0.0435 mol) were mixed with carbon tetrachloride (50 ml), 2,2'-azobisisobutyronitrile (AIBN, 0.16 g, 1 mmol) as a radical initiator was added thereto, and the mixture was stirred and heated for 12 hours. The reacting solution was cooled, the succinimide was filtered out, and the solvent was removed under a reduced pressure. The resulting residue was subjected to silica gel column chromatography (ethyl acetate:n-hexane=1:4) to obtain the title compound as a colorless liquid (11.16 g, 90%).
$^1$H-NMR (CDCl$_3$, TMS) d (ppm): 7.62-7.01 (m, 4H), 4.39 (s, 2H), 4.04 (s, 3H), 3.85 (s, 3H)

<Preparation of the Compound of Formula (III)>

Preparation Example 2

Preparation of 3-(2,2-dichlorovinyl)phenol

Step 1) Preparation of 3-(2,2,2-trichloro-1-hydroxyethyl)phenol

Aluminum (8.06 g, 0.3 mol) and lead bromide (3.7 g, 0.01 mmol) were added to a mixture of 3-hydroxy benzaldehyde (12.3 g, 0.1 mol) was mixed with 200 ml of dimethylformamide. Carbon tetrachloride (61.53 g, 0.4 mol) was slowly added thereto, the mixture was stirred at room temperature for 10 hours, and unreacted solid was filtered to remove therefrom. After sequentially adding 5% HCl, ethylacetate and water thereto, the mixture was extracted three times with ethyl acetate. The combined organic layer was dried over anhydrous magnesium sulfate, filtered and distilled. The resulting residue was subjected to column chromatography (ethyl acetate:n-hexane=1:4) to obtain the title compound (12.57 g, 91%).

$^1$H-NMR (CDCl$_3$, TMS) d (ppm): 5.49 (s, 1H), 6.68-7.02 (m, 4H)

Step 2) Preparation of 3-(2,2-dichlorovinyl)phenol

Aluminum (3.73 g, 0.091 mol), lead bromide (2.28 g, 0.0091 mol) and 36% HC (15.47 ml, 0.182 mol) were added to 200 ml of methanol, and 3-(2,2,2-trichloro-1-hydroxyethyl)phenol (12.57 g, 0.091 mol) obtained in Step 1 was added thereto. The mixture was stirred at 60° C. for 4 hours. The solvent was removed therefrom under a reduced pressure. Ice was added to the reaction mixture and resulting mixture was washed three times with n-hexane and ether (1:1). The organic layer was dried over anhydrous magnesium sulfate, filtered and distilled under a reduced pressure. The resulting residue was subjected to silica gel column chromatography (ethyl acetate:n-hexane=1:9) to obtain the title compound (16.0 g, 93%).

$^1$H-NMR (CDCl$_3$, TMS) d (ppm): 7.26 (s, 1H), 6.78-7.47 (m, 4H)

Preparation Examples 3 to 20

The procedure of Preparation Example 2 was repeated except for using each of the corresponding starting materials instead of 3-hydroxybenzaldehyde, and using each of the corresponding halocarbon instead of CCl$_4$ to obtain the compounds of formula 3 shown in Table 1.

TABLE 1

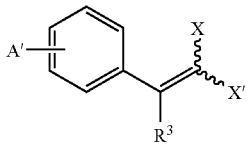

| Prep. Ex. | X | X' | A' | R$^3$ | $^1$H-NMR(CDCl$_3$, TMS) δ (ppm) |
|---|---|---|---|---|---|
| 3 | Br | Br | 3-OH | H | 6.78-7.47(m, 4 H), 7.63(s, 1H) |
| 4 | F | Cl | 3-OH | H | 6.36(dd, 1 H), 6.61-7.09(m, 4 H) |
| 5 | Cl | Br | 3-OH | H | 7.2(d,1 H), 6.69-7.50(m, 4 H) |
| 6 | Cl | Cl | 4-OH | H | 6.68-7.13(m, 4 H), 6.94(s, 1 H) |
| 7 | Br | Br | 4-OH | H | 6.63-7.27(m, 4 H), 7.63(s, 1 H) |
| 8 | F | F | 4-OH | H | 5.21(s, 1 H), 6.69-7.51(m, 4 H) |
| 9 | F | Cl | 4-OH | H | 5.79(d, 1 H), 6.61-7.29(m, 4 H) |
| 10 | Cl | Br | 4-OH | H | 6.69-7.21(m, 4 H), 7.36(d, 1 H) |
| 11 | Cl | Cl | 3-CH$_3$CO | H | 2.55(s, 3 H), 6.94(s, 1 H), 6.78-7.47(m, 4 H) |
| 12 | Br | Br | 3-CH$_3$CO | H | 2.59(s, 3 H), 7.53(s, 1 H), 7.40-8.02(m, 4 H) |
| 13 | F | F | 3-CH$_3$CO | H | 2.61(s, 3 H), 5.23(d, 1 H), 7.38-7.98(m, 4 H) |
| 14 | F | Cl | 3-CH$_3$CO | H | 2.54(s, 3 H), 5.79(dd, 1 H), 6.61-7.09(m, 4 H) |
| 15 | Cl | Br | 3-CH$_3$CO | H | 2.60(s, 3 H), 7.36(d, 1 H), 6.69-7.50(m, 4 H) |
| 16 | Cl | Cl | 4-CH$_3$CO | H | 2.54(s, 3 H), 6.94(s, 1 H), 6.78-7.47(m, 4 H) |

TABLE 1-continued

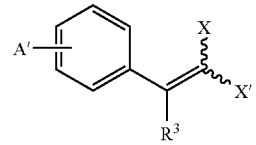

| Prep. Ex. | X | X' | A' | R$^3$ | $^1$H-NMR(CDCl$_3$, TMS) δ (ppm) |
|---|---|---|---|---|---|
| 17 | Br | Br | 4-CH$_3$CO | H | 2.58(s, 3 H), 7.38(s, 1 H), 7.40-8.02(m, 4 H) |
| 18 | F | F | 4-CH$_3$CO | H | 2.61(s, 3 H), 5.23(d, 1 H), 7.38-7.98(m, 4 H) |
| 19 | F | Cl | 4-CH$_3$CO | H | 2.54(s, 3 H), 5.79(dd, 1 H), 6.78-7.09(m, 4 H) |
| 20 | Cl | Br | 4-CH$_3$CO | H | 2.60(s, 3 H), 7.36(d, 1 H), 6.69-7.48(m, 4 H) |

Preparation Example 21

Preparation of 1-(3-(2,2-dichlorovinyl)phenyl)ethane-1-oneoxime

A mixture of 1-(3-(2,2-dichlorovinyl)phenyl)ethanone (10.75 g, 50 mmol) obtained in Preparation Example 11 and hydroxylamine hydrochloride (3.48 g, 50 mmol) was added in 100 ml of methanol. Pyridine (4.05 ml, 50 mmol) was added thereto, and the mixture was refluxed for 1 hour. After adding water thereto, the mixture was washed with 30 ml of ethylacetate three times. The combined organic layer was dried over anhydrous magnesium sulfate, filtered and distilled. The resulting residue was subjected to column chromatography (ethyl acetate:n-hexane=1:4) to obtain the title compound (9.79 g, 91%).

$^1$H-NMR (CDCl$_3$, TMS) δ (ppm): 7.26 (s, 1H), 6.78-7.47 (m, 4H)

Preparation Examples 22 to 30

The procedure of Preparation Example 21 was repeated except for using each of the corresponding intermediate compounds obtained in Preparation Example 12 to 20 instead of 1-(3-(2,2-dichlorovinyl)phenyl)ethanone obtained in Preparation Example 11 shown in Table 2.

TABLE 2

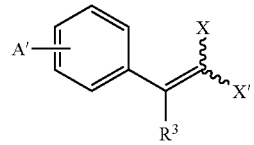

| Prep. Ex. | X | X' | A' | R$^3$ | $^1$H-NMR(CDCl$_3$, TMS) δ (ppm) |
|---|---|---|---|---|---|
| 22 | Br | Br | 3-CH$_3$C=NOH | H | 2.26(s, 3 H), 7.68(s, 1 H), 7.13-7.62(m, 4 H) |
| 23 | F | F | 3-CH$_3$C=NOH | H | 2.18(s, 3 H), 5.67(s, 1 H), 7.16-7.48(m, 4 H) |
| 24 | F | Cl | 3-CH$_3$C=NOH | H | 2.25(s, 3 H), 6.38(s, 1 H), 7.15-7.52(m, 4 H) |
| 25 | Cl | Br | 3-CH$_3$C=NOH | H | 2.24(s, 3 H), 7.21(s, 1 H), 7.22-7.67(m, 4 H) |
| 26 | Cl | Cl | 4-CH$_3$C=NOH | H | 2.21(s, 3 H), 6.94(s, 1 H), 7.18-7.51(m, 4 H) |
| 27 | Br | Br | 4-CH$_3$C=NOH | H | 2.26(s, 3 H), 7.69(s, 1 H), 7.14-7.63(m, 4 H) |

TABLE 2-continued

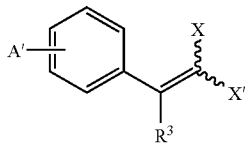

| Prep. Ex. | X | X' | A' | R³ | ¹H-NMR(CDCl₃, TMS) δ (ppm) |
|---|---|---|---|---|---|
| 28 | F | F | 4-CH₃C=NOH | H | 2.18(s, 3 H), 5.66(s, 1 H), 7.16-7.47(m, 4 H) |
| 29 | F | Cl | 4-CH₃C=NOH | H | 2.24(s, 3 H), 6.37(s, 1 H), 7.15-7.52(m, 4 H) |
| 30 | Cl | Br | 4-CH₃C=NOH | H | 2.24(s, 3 H), 7.21(s, 1 H), 7.22-7.67(m, 4 H) |

Preparation Example 31

Preparation of 2-chloro-4-(2,2-dichlorovinyl)phenol

Step 1) Preparation of 2-chloro-4-(2,2,2-trichloro-1-hydroxyethyl)phenol

3-Chloro-4-hydroxy benzaldehyde (15.6 g, 0.1 mol) was added to 200 ml of dimethylformamide, a mixture was stirred, aluminium (8.09 g, 0.3 mol) and leadbromide (3.67 g, 0.01 mmol) were added thereto. CCl₄ (61.53 g, 0.4 mol) was slowly added to the reaction mixture. The mixture was stirred at room temperature for 10 hours, and unreacted solid was filtered to remove therefrom. After sequentially adding 5% HCl, ethylacetate and water thereto, the mixture was extracted three times with ethyl acetate. The combined organic layer was dried over anhydrous magnesium sulfate, filtered and distilled. The resulting residue was subjected to column chromatography (ethyl acetate: n-hexane=1:4) to obtain the title compound (24.55 g, 89%).

¹H-NMR (CDCl₃, TMS) δ (ppm): 3.33 (s, 1H), 5.14 (s, 1H), 5.72 (s, 1H), 7.00-7.62 (m, 3H)

Step 2) Preparation of 2-chloro-4-(2,2-dichlorovinyl)phenol

Aluminium (3.64 g, 0.089 mol), leadbromide (2.23 g, 0.0089 mol) and 36% HCl (15.13 ml, 0.178 mol) were added to 200 ml of methanol, the mixture was stirred, and 2-chloro-4-(2,2,2-trichloro-1-hydroxyethyl)phenol (24.55 g, 0.089 mol) obtained in Step 1 was added thereto. The mixture was stirred at 60° C. for 4 hours. The solvent was removed therefrom under a reduced pressure. Ice was added to the reaction mixture and resulting mixture was washed three times with n-hexane and ether (1:1). The organic layer was dried over anhydrous magnesium sulfate, filtered and distilled under a reduced pressure. The resulting residue was subjected to column chromatography (ethyl acetate:n-hexane=1:4) to obtain the title compound (17.3 g, 87%).

¹H-NMR (CDCl₃, TMS) δ (ppm): 5.65 (s, 1H), 6.73 (s, 1H), 6.99-7.59 (m, 3H)

Preparation Examples 32 to 54

The procedure of Preparation Example 31 was repeated except for using each of the corresponding starting materials instead of 3-chloro-4-hydroxybenzaldehyde to obtain the compounds of formula 3 shown in Table 3.

TABLE 3

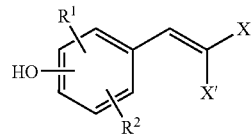

| Prep. Ex. | X | X' | OH | R¹ | R² | ¹H-NMR (CDCl₃, TMS) (PPM) |
|---|---|---|---|---|---|---|
| 32 | Cl | Cl | 4-position | 2-methyl | H | 2.25(s, 3 H), 4.88(s, 1 H), 6.74-7.33(m, 4 H) |
| 33 | Cl | Cl | 3-position | 2-Cl | H | 5.63(s, 1 H), 7.20-7.45(m, 4 H) |
| 34 | Cl | Cl | 2-position | 4-methyl | H | 2.31(s, 3 H), 5.35(s, 1 H), 6.71-7.39(m, 4 H) |
| 35 | Cl | Cl | 3-position | 2-methoxy | H | 3.90(s, 3 H), 5.63(s, 1 H), 6.74-7.26(m, 4 H) |
| 36 | Cl | Cl | 2-position | 6-methyl | H | 2.35(s, 3 H), 5.27(s, 1 H), 6.67-7.21(m, 4 H) |
| 37 | Cl | Cl | 3-position | 2-Br | 6-methoxy | 3.73(s, 3 H), 5.63(s, 1 H), 6.49-7.42(m, 3 H) |
| 38 | Cl | Cl | 4-position | 2-Br | H | 5.92(s, 1 H), 6.84-7.34(m, 4 H) |
| 39 | Cl | Cl | 2-position | 4-F | H | 5.47(s, 1 H), 6.90-7.25(m, 4 H) |
| 40 | Cl | Cl | 4-position | 3-Cl | H | 5.55(s, 1 H), 7.01-7.44(m, 4 H) |
| 41 | Cl | Cl | 4-position | 2-ethoxy | H | 1.36(t, 3 H) 3.90(m, 2 H), 5.44(s, 1 H), 6.74-7.26(m, 4 H) |
| 42 | Cl | Cl | 2-position | 5-Br | H | 5.72(s, 1 H), 6.64-7.24(m, 4 H) |
| 43 | Br | Br | 4-position | 2-Cl | H | 5.45(s, 1 H), 6.92-7.33(m, 4 H) |
| 44 | Br | Br | 4-position | 2-methyl | H | 2.25(s, 3 H), 4.88(s, 1 H), 6.74-7.33(m, 4 H) |
| 45 | Br | Br | 3-position | 2-Cl | H | 5.63(s, 1 H), 7.20-7.45(m, 4 H) |
| 46 | Br | Br | 2-position | 4-methyl | H | 2.31(s, 3 H), 5.35(s, 1 H), 6.71-7.39(m, 4 H) |
| 47 | Br | Br | 3-position | 2-methoxy | H | 3.90(s, 3 H), 5.63(s, 1 H), 6.74-7.26(m, 4 H) |
| 48 | Br | Br | 2-position | 6-methyl | H | 2.35(s, 3 H), 5.27(s, 1 H), 6.67-7.21(m, 4 H) |
| 49 | Br | Br | 3-position | 2-Br | 6-methoxy | 3.73(s, 3 H), 5.63(s, 1 H), 6.49-7.42(m, 3 H) |
| 50 | Br | Br | 4-position | 2-Br | H | 5.92(s, 1 H), 6.84-7.34(m, 4 H) |
| 51 | Br | Br | 2-position | 4-F | H | 5.47(s, 1 H), 6.90-7.25(m, 4 H) |
| 52 | Br | Br | 4-position | 3-Cl | H | 5.55(s, 1 H), 7.01-7.44(m, 4 H) |
| 53 | Br | Br | 4-position | 2-ethoxy | H | 1.36(t, 3 H), 3.90(s, 2 H), 5.44(s, 1 H), 6.74-7.26(m, 4 H) |
| 54 | Br | Br | 2-position | 5-Br | 11 | 5.72(s, 1 H), 6.64-7.24(m, 4 H) |

Example 1

Preparation of methyl-(E)-2-(2-((3-(2,2-dichlorovinyl)phenoxy)methyl)phenyl)-2-methoxyiminoacetate 3-(2,2-Dichlorovinyl)phenol (1.44 g, 7.6 mmol) obtained in Preparation Example 2 was dissolved in 50 ml of acetonitrile, potassium carbonate (2.1 g, 15.2 mmol) was added thereto, and the mixture was stirred for 30 minutes. methyl-(2E)-2-methoxyimino-2-(2'-bromomethyl)phenylacetate (3.0 g, 7.6 mmol) obtained in Preparation Example 1 was added to the reaction mixture and the mixture was refluxed for 5 hours. After completion of the reaction, unreacted solid was filtered to remove therefrom, and the filtrate was distilled under a reduced pressure. The resulting residue was subjected to column chromatography (ethyl acetate:n-hexane=1:4) to obtain the title compound (2.63 g, 88%).

$^1$H-NMR (CDCl$_3$, TMS) δ(ppm): 3.88 (s, 3H), 4.04 (s, 3H), 4.97 (s, 2H), 6.73 (s, 1H), 6.89-7.54 (m, 8H)

Example 2

Preparation of (E)-2-(2-((3-(2,2-dichlorovinyl)phenoxy)methyl)phenyl)-2-methoxyimino-N-methylacetamide Methyl-(E)-2-(2-((3-(2,2-dichlorovinyl)phenoxy)methyl)phenyl)-2-methoxyiminoacetate (0.4 g, 1 mmol) obtained in Example 1 was added to 10 ml of methanol. 40% methylamine solution (0.39 g, 5 mmol) was slowly added thereto, and the mixture was stirred at room temperature for 6 hours. The solvent was removed therefrom under a reduced pressure. After adding water thereto, the mixture was extracted three times with ethyl acetate. The combined organic layer was dried over anhydrous magnesium sulfate, filtered and distilled under a reduced pressure. The resulting residue was subjected to column chromatography (ethyl acetate:n-hexane=1:4) to obtain the title compound (0.35 g, 89%).

$^1$H-NMR (CDCl$_3$, TMS) δ (ppm): 2.81 (s, 3H), 3.93 (s, 3H), 4.97 (s, 2H), 6.71 (s, 1H), 6.88-7.51 (m, 8H)

Example 3

Preparation of methyl-(E)-2-(2-((4-(2,2-dichlorovinyl)phenoxy)methyl)phenyl)-2-methoxyiminoacetate The procedure of Example 1 was repeated except for using 4-(2,2-dichlorovinyl)phenol (1.44 g, 7.6 mmol) instead of 3-(2,2-dichlorovinyl)phenol to obtain the title compound (2.73 g, 91%).

$^1$H-NMR (CDCl$_3$, TMS) δ (ppm): 3.87 (s, 3H), 4.02 (s, 3H), 4.97 (s, 2H), 6.77 (s, 1H), 6.88-7.54 (m, 8H)

Example 4

Preparation of (E)-2-(2-((4-(2,2-dichlorovinyl)phenoxy)methyl)phenyl)-2-methoxyimino-N-methylacetamide The procedure of Example 2 was repeated except for using methyl-(E)-2-(2-((4-(2,2-dichlorovinyl)phenoxy)methyl)phenyl)-2-methoxyiminoacetate (0.39 g, 1 mmol) obtained in Example 3 instead of methyl-(E)-2-(2-((3-(2,2-dichlorovinyl)phenoxy)methyl)phenyl)-2-methoxyiminoacetate to obtain the title compound (0.37 g, 94%).

$^1$H-NMR (CDCl$_3$, TMS) δ (ppm): 2.80 (s, 3H), 3.93 (s, 3H), 4.96 (s, 2H), 6.71 (s, 1H), 6.78-7.50 (m, 8H)

Example 5

Preparation of methyl-(E)-2-(2-((3-(2,2-dibromovinyl)phenoxy)methyl)phenyl)-2-methoxyiminoacetate The procedure of Example 1 was repeated except for using 3-(2,2-dibromovinyl)phenol (2.0 g, 7.2 mmol) instead of 3-(2,2-dichlorovinyl)phenol to obtain the title compound (3.03 g, 87%).

$^1$H-NMR (CDCl$_3$, TMS) δ (ppm): 3.86 (s, 3H), 4.02 (s, 3H), 4.95 (s, 2H), 6.79 (d, 1H), 7.04-7.59 (m, 8H)

Example 6

Preparation of (E)-2-(2-((3-(2,2-dibromovinyl)phenoxy)methyl)phenyl)-2-methoxyimino-N-methylacetamide The procedure of Example 2 was repeated except for using methyl-(E)-2-(2-((3-(2,2-dibromovinyl)phenoxy)methyl)phenyl)-2-methoxyiminoacetate (0.48 g, 1 mmol) obtained in Example 5 instead of methyl-(E)-2-(2-((3-(2,2-dichlorovinyl)phenoxy)methyl)phenyl)-2-methoxyiminoacetate to obtain the title compound (0.415 g, 86%).

$^1$H-NMR (CDCl$_3$, TMS) δ (ppm): 2.84 (d, 3H), 3.94 (s, 3H), 4.98 (s, 2H), 6.76 (d, 1H), 7.11-7.53 (m, 8H)

Example 7

Preparation of methyl-(E)-2-(2-((4-(2,2-dibromovinyl)phenoxy)methyl)phenyl)-2-methoxyiminoacetate The procedure of Example 1 was repeated except for using 4-(2,2-dibromovinyl)phenol (2.0 g, 7.2 mmol) instead of 3-(2,2-dichlorovinyl)phenol to obtain the title compound (2.89 g, 87%).

$^1$H-NMR (CDCl$_3$, TMS) δ (ppm): 3.82 (s, 3H), 4.00 (s, 3H), 4.95 (s, 2H), 6.84 (s, 1H), 6.88-7.49 (m, 8H)

Example 8

Preparation of (E)-2-(2-((4-(2,2-dibromovinyl)phenoxy)methyl)phenyl)-2-methoxyimino-N-methylacetamide The procedure of Example 2 was repeated except for using methyl-(E)-2-(2-((4-(2,2-dibromovinyl)phenoxy)methyl)phenyl)-2-methoxyiminoacetate (0.48 g, 1 mmol) obtained in Example 7 instead of methyl-(E)-2-(2-((3-(2,2-dichlorovinyl)phenoxy)methyl)phenyl)-2-methoxyiminoacetate to obtain the title compound (0.425 g, 88%).

$^1$H-NMR (CDCl$_3$, TMS) δ (ppm): 2.87 (d, 3H), 3.95 (s, 3H), 4.96 (s, 2H), 6.84 (d, 1H), 7.22-7.51 (m, 8H)

Example 9

Preparation of methyl-(E)-2-(2-((4-(2,2-difluorovinyl)phenoxy)methyl)phenyl)-2-methoxyiminoacetate The procedure of Example 1 was repeated except for using 4-(2,2-difluorovinyl)phenol (1.56 g, 10 mmol) instead of 3-(2,2-dichlorovinyl)phenol to obtain the title compound (3.35 g, 93%).

$^1$H-NMR (CDCl$_3$, TMS) δ (ppm): 3.84 (s, 3H), 4.11 (s, 3H), 4.97 (s, 2H), 5.23 (d, 1H), 6.78-7.46 (m, 8H)

Example 10

Preparation of (E)-2-(2-((4-(2,2-difluorovinyl)phenoxy)methyl)phenyl)-2-methoxyimino-N-methylacetamide The procedure of Example 2 was repeated except for using methyl-(E)-2-(2-((4-(2,2-difluorovinyl)phenoxy)methyl)phenyl)-2-methoxyiminoacetate (0.36 g, 1 mmol) obtained in Example 9 instead of methyl-(E)-2-(2-((3-(2,2-dichlorovinyl)phenoxy)methyl)phenyl)-2-methoxyiminoacetate to obtain the title compound (0.343 g, 95%).
$^1$H-NMR (CDCl$_3$, TMS) δ (ppm): 2.82 (d, 3H), 3.93 (s, 3H), 4.97 (s, 2H), 5.21 (d, 1H), 6.68-7.54 (m, 8H)

Example 11

Preparation of methyl-(2E)-2-(2-((3-(2-chloro-2-fluorovinyl)phenoxy)methyl)phenyl)-2-methoxyiminoacetate The procedure of Example 1 was repeated except for using 3-(2-chloro-2-fluorovinyl)phenol (1.73 g, 10 mmol) instead of 3-(2,2-dichlorovinyl)phenol to obtain the title compound (2.87 g, 76%).
$^1$H-NMR (CDCl$_3$, TMS) δ (ppm): 3.67 (s, 3H), 4.01 (s, 3H), 5.21 (s, 2H), 5.79 (d, 1H), 6.65-7.72 (m, 8H)

Example 12

Preparation of (2E)-2-(2-((3-(2-chloro-2-difluorovinyl)phenoxy)methyl)phenyl)-2-methoxyimino-N-methylacetamide The procedure of Example 2 was repeated except for using methyl-(2E)-2-(2-((3-(2-chloro-2-fluorovinyl)phenoxy)methyl)phenyl)-2-methoxyiminoacetate (0.38 g, 1 mmol) obtained in Example 11 instead of methyl-(E)-2-(2-((3-(2,2-dichlorovinyl)phenoxy)methyl)phenyl)-2-methoxyiminoacetate to obtain the title compound (0.314 g, 83%).
$^1$H-NMR (CDCl$_3$, TMS) δ (ppm): 2.78 (d, 3H), 3.93 (s, 3H), 5.07 (s, 2H), 5.78 (d, 1H), 6.68-7.66 (m, 8H)

Example 13

Preparation of methyl-(2E)-2-(2-((4-(2-chloro-2-fluorovinyl)phenoxy)methyl)phenyl)-2-methoxyiminoacetate The procedure of Example 1 was repeated except for using 4-(2-chloro-2-fluorovinyl)phenol (1.73 g, 10 mmol) instead of 3-(2,2-dichlorovinyl)phenol to obtain the title compound (2.95 g, 78%).
$^1$H-NMR (CDCl$_3$, TMS) δ (ppm): 3.69 (s, 3H), 4.02 (s, 3H), 5.18 (s, 2H), 5.82 (d, 1H), 6.65-7.72 (m, 8H)

Example 14

Preparation of (2E)-2-(2-((4-(2-chloro-2-difluorovinyl)phenoxy)methyl)phenyl)-2-methoxyimino-N-methylacetamide The procedure of Example 2 was repeated except for using methyl-(2E)-2-(2-((4-(2-chloro-2-fluorovinyl)phenoxy)methyl)phenyl)-2-methoxyiminoacetate (0.38 g, 1 mmol) obtained in Example 13 instead of methyl-(E)-2-(2-((3-(2,2-dichlorovinyl)phenoxy)methyl)phenyl)-2-methoxyiminoacetate to obtain the title compound (0.337 g, 89%).
$^1$H-NMR (CDCl$_3$, TMS) δ (ppm): 2.78 (d, 3H), 3.93 (s, 3H), 5.07 (s, 2H), 5.78 (d, 1H), 6.68-7.62 (m, 8H)

Example 15

Preparation of methyl-(2E)-2-(2-((3-(2-bromo-2-chlorovinyl)phenoxy)methyl)phenyl)-2-methoxyiminoacetate The procedure of Example 1 was repeated except for using 3-(2-bromo-2-chlorovinyl)phenol (1.17 g, 5 mmol) instead of 3-(2,2-dichlorovinyl)phenol to obtain the title compound (1.78 g, 81%).
$^1$H-NMR (CDCl$_3$, TMS) δ (ppm): 3.67 (s, 3H), 4.01 (s, 3H), 5.19 (s, 2H), 7.36 (d, 1H), 6.71-7.72 (m, 8H)

Example 16

Preparation of (2E)-2-(2-((3-(2-bromo-2-chlorovinyl)phenoxy)methyl)phenyl)-2-methoxyimino-N-methylacetamide The procedure of Example 2 was repeated except for using methyl-(2E)-2-(2-((3-(2-bromo-2-chlorovinyl)phenoxy)methyl)phenyl)-2-methoxyiminoacetate (0.44 g, 1 mmol) obtained in Example 15 instead of methyl-(E)-2-(2-((3-(2,2-dichlorovinyl)phenoxy)methyl)phenyl)-2-methoxyiminoacetate to obtain the title compound (0.337 g, 89%).
$^1$H-NMR (CDCl$_3$, TMS) δ (ppm): 2.74 (d, 3H), 4.01 (s, 3H), 5.20 (s, 2H), 7.36 (d, 1H), 6.68-7.72 (m, 8H)

Example 17

Preparation of methyl-(2E)-2-(2-((4-(2-bromo-2-chlorovinyl)phenoxy)methyl)phenyl)-2-methoxyiminoacetate The procedure of Example 1 was repeated except for using 4-(2-bromo-2-chlorovinyl)phenol (1.17 g, 5 mmol) instead of 3-(2,2-dichlorovinyl)phenol to obtain the title compound (1.71 g, 78%).
$^1$H-NMR (CDCl$_3$, TMS) δ (ppm): 3.82 (s, 3H), 4.08 (s, 3H), 5.08 (s, 2H), 7.31 (d, 1H), 6.67-7.62 (m, 8H)

Example 18

Preparation of (2E)-2-(2-((4-(2-bromo-2-chlorovinyl)phenoxy)methyl)phenyl)-2-methoxyimino-N-methylacetamide The procedure of Example 2 was repeated except for using methyl-(2E)-2-(2-((4-(2-bromo-2-chlorovinyl)phenoxy)methyl)phenyl)-2-methoxyiminoacetate (0.44 g, 1 mmol) obtained in Example 17 instead of methyl-(E)-2-(2-((3-(2,2-dichlorovinyl)phenoxy)methyl)phenyl)-2-methoxyiminoacetate to obtain the title compound (0.345 g, 91%).
$^1$H-NMR (CDCl$_3$, TMS) δ (ppm): 2.81 (d, 3H), 4.21 (s, 3H), 5.20 (s, 2H), 7.35 (d, 1H), 6.68-7.72 (m, 8H)

Example 19

Preparation of methyl-(E)-2-[[[[2-[3-(2,2-dichlorovinyl)phenyl](1-methyl)methylidene]amino]oxy]methyl]phenyl]-2-methoxyiminoacetate The procedure of Example 1 was repeated except for using 1-(3-(2,2-dichlorovinyl)phenyl)ethane-1-oneoxime (1.15 g, 5 mmol) instead of 3-(2,2-dichlorovinyl)phenol to obtain the title compound (1.76 g, 81%).

¹H-NMR (CDCl₃, TMS) δ (ppm): 2.08 (s, 3H), 3.74 (s, 3H), 4.03 (s, 3H), 4.96 (s, 2H), 6.95 (s, 1H), 7.27-7.72 (m, 8H)

Example 20

Preparation of (E)-2-[[[[[2-[3-(2,2-dichlorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[3-(2,2-dichlorovinyl)phenyl](1-methyl)methylidene]amino]oxy]methyl]phenyl]-2-methoxyiminoacetate (0.436 g, 1 mmol) obtained in Example 19 instead of methyl-(E)-2-(2-((3-(2,2-dichlorovinyl)phenoxy)methyl)phenyl)-2-methoxyiminoacetate to obtain the title compound (0.404 g, 93%).

¹H-NMR (CDCl₃, TMS) δ0 (ppm): 2.11 (s, 3H), 2.87 (d, 3H), 3.80 (s, 3H), 5.01 (s, 2H), 6.94 (d, 1H), 7.23-7.51 (m, 8H)

Example 21

Preparation of methyl-(E)-2-[[[[[2-[4-(2,2-dichlorovinyl)phenyl](1-methyl)methylidene]amino]oxy]methyl]phenyl]-2-methoxyiminoacetate The procedure of Example 1 was repeated except for using 1-(4-(2,2-dichlorovinyl)phenyl)ethane-1-oneoxime (1.15 g, 5 mmol) instead of 3-(2,2-dichlorovinyl)phenol to obtain the title compound (1.74 g, 80%).

¹H-NMR (CDCl₃, TMS) δ (ppm): 2.09 (s, 3H), 3.84 (s, 3H), 4.03 (s, 3H), 4.96 (s, 2H), 6.95 (s, 1H), 7.27-7.72 (m, 8H)

Example 22

Preparation of (E)-2-[[[[[2-[4-(2,2-dichlorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[4-(2,2-dichlorovinyl)phenyl](1-methyl)methylidene]amino]oxy]methyl]phenyl]-2-methoxyimino acetate (0.436 g, 1 mmol) obtained in Example 21 instead of methyl-(E)-2-(2-((3-(2,2-dichlorovinyl)phenoxy)methyl)phenyl)-2-methoxyiminoacetate to obtain the title compound (0.391 g, 90%).

¹H-NMR (CDCl₃, TMS) δ (ppm): 2.23 (s, 3H), 2.87 (d, 3H), 3.99 (s, 3H), 5.01 (s, 2H), 6.97 (d, 1H), 7.27-7.78 (m, 8H)

Example 23

Preparation of methyl-(E)-2-[[[[[2-[3-(2,2-dibromovinyl)phenyl](1-methyl)methylidene]amino]oxy]methyl]phenyl]-2-methoxyiminoacetate The procedure of Example 1 was repeated except for using 1-(3-(2,2-dibromovinyl)phenyl)ethane-1-oneoxime (1.6 g, 5 mmol) instead of 3-(2,2-dichlorovinyl)phenol to obtain the title compound (2.31 g, 86%).

¹H-NMR (CDCl₃, TMS) δ (ppm): 2.17 (s, 3H), 3.80 (s, 3H), 4.01 (s, 3H), 5.09 (s, 2H), 7.25 (s, 1H), 7.17-7.52 (m, 8H)

Example 24

Preparation of (E)-2-[[[[[2-[3-(2,2-dibromovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[3-(2,2-dibromovinyl)phenyl](1-methyl)methylidene]amino]oxy]methyl]phenyl]-2-methoxyiminoacetate (0.54 g, 1 mmol) obtained in Example 23 instead of methyl-(E)-2-(2-((3-(2,2-dichlorovinyl)phenoxy)methyl)phenyl)-2-methoxyiminoacetate to obtain the title compound (0.478 g, 89%).

¹H-NMR (CDCl₃, TMS) δ (ppm): 2.23 (s, 3H), 2.88 (d, 3H), 4.00 (s, 3H), 5.13 (s, 2H), 7.24 (d, 1H), 7.18-7.49 (m, 8H)

Example 25

Preparation of methyl-(E)-2-[[[[[2-[4-(2,2-dibromovinyl)phenyl](1-methyl)methylidene]amino]oxy]methyl]phenyl]-2-methoxyiminoacetate The procedure of Example 1 was repeated except for using 1-(4-(2,2-dibromovinyl)phenyl)ethane-1-oneoxime (1.6 g, 5 mmol) instead of 3-(2,2-dichlorovinyl)phenol to obtain the title compound (2.34 g, 87%).

¹H-NMR (CDCl₃, TMS) δ (ppm): 2.24 (s, 3H), 3.79 (s, 3H), 4.02 (s, 3H), 5.12 (s, 2H), 7.25 (s, 1H), 7.17-7.50 (m, 8H)

Example 26

Preparation of (E)-2-[[[[[2-[4-(2,2-dibromovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[4-(2,2-dibromovinyl)phenyl](1-methyl)methylidene]amino]oxy]methyl]phenyl]-2-methoxyiminoacetate (0.54 g, 1 mmol) obtained in Example 25 instead of methyl-(E)-2-(2-((3-(2,2-dichlorovinyl)phenoxy)methyl)phenyl)-2-methoxyiminoacetate to obtain the title compound (0.467 g, 87%).

¹H-NMR (CDCl₃, TMS) δ (ppm): 2.18 (s, 3H), 2.87 (d, 3H), 3.98 (s, 3H), 5.08 (s, 2H), 7.24 (d, 1H), 7.18-7.51 (m, 8H)

Example 27

Preparation of methyl-(E)-2-[[[[[2-[3-(2,2-difluorovinyl)phenyl](1-methyl)methylidene]amino]oxy]methyl]phenyl]-2-methoxyiminoacetate The procedure of Example 1 was repeated except for using 1-(3-(2,2-difluorovinyl)phenyl)ethane-1-oneoxime (1.0 g, 5 mmol) instead of 3-(2,2-dichlorovinyl)phenol to obtain the title compound (1.57 g, 78%).

¹H-NMR (CDCl₃, TMS) δ (ppm): 2.18 (s, 3H), 3.69 (s, 3H), 4.02 (s, 3H), 5.20 (s, 2H), 5.63 (s, 1H), 6.87-7.45 (m, 8H)

Example 28

Preparation of (E)-2-[[[[[2-[3-(2,2-difluorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[3-(2,2-difluorovinyl)phenyl](1-methyl)methylidene]amino]oxy]methyl]phenyl]-2-methoxyiminoacetate (0.40 g, 1 mmol) obtained in Example 27 instead of methyl-(E)-2-(2-((3-(2,2-dichlorovinyl)phenoxy)methyl)phenyl)-2-methoxyiminoacetate to obtain the title compound (0.334 g, 83%).
$^1$H-NMR (CDCl$_3$, TMS) δ (ppm): 2.24 (s, 3H), 2.82 (d, 3H), 3.98 (s, 3H), 5.21 (s, 2H), 5.64 (d, 1H), 6.88-7.46 (m, 8H)

Example 29

Preparation of methyl-(E)-2-[[[[[2-[4-(2,2-difluorovinyl)phenyl](1-methyl)methylidene]amino]oxy]methyl]phenyl]-2-methoxyiminoacetate The procedure of Example 1 was repeated except for using 1-(4-(2,2-difluorovinyl)phenyl)ethane-1-oneoxime (1.0 g, 5 mmol) instead of 3-(2,2-dichlorovinyl)phenol to obtain the title compound (1.63 g, 81%).
$^1$H-NMR (CDCl$_3$, TMS) δ (ppm): 2.19 (s, 3H), 3.69 (s, 3H), 4.01 (s, 3H), 5.22 (s, 2H), 5.67 (s, 1H), 6.80-7.55 (m, 8H)

Example 30

Preparation of (E)-2-[[[[[2-[4-(2,2-difluorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[4-(2,2-difluorovinyl)phenyl](1-methyl)methylidene]amino]oxy]methyl]phenyl]-2-methoxyiminoacetate (0.40 g, 1 mmol) obtained in Example 29 instead of methyl-(E)-2-(2-((3-(2,2-dichlorovinyl)phenoxy)methyl)phenyl)-2-methoxyiminoacetate to obtain the title compound (0.330 g, 82%).
$^1$H-NMR (CDCl$_3$, TMS) δ (ppm): 2.21 (s, 3H), 2.84 (d, 3H), 3.98 (s, 3H), 5.19 (s, 2H), 5.63 (d, 1H), 6.87-7.48 (m, 8H)

Example 31

Preparation of methyl-(E)-2-[[[[[2-[3-(2-chloro-2-fluorovinyl)phenyl](1-methyl)methylidene]amino]oxy]methyl]phenyl]-2-methoxyiminoacetate The procedure of Example 1 was repeated except for using 1-(3-(2-chloro-2-fluorovinyl)phenyl)ethane-1-oneoxime (1.07 g, 5 mmol) instead of 3-(2,2-dichlorovinyl)phenol to obtain the title compound (1.78 g, 85%).
$^1$H-NMR (CDCl$_3$, TMS) δ (ppm): 2.24 (d, 3H), 3.69 (s, 3H), 3.87 (s, 3H), 5.20 (s, 2H), 6.37 (s, 1H), 7.17-7.50 (m, 8H)

Example 32

Preparation of (E)-2-[[[[[2-[3-(2-chloro-2-fluorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[3-(2-chloro-2-fluorovinyl)phenyl](1-methyl)methylidene]amino]oxy]methyl]phenyl]-2-methoxyiminoacetate (0.42 g, 1 mmol) obtained in Example 31 instead of methyl-(E)-2-(2-((3-(2,2-dichlorovinyl)phenoxy)methyl)phenyl)-2-methoxyiminoacetate to obtain the title compound (0.369 g, 88%).
$^1$H-NMR (CDCl$_3$, TMS) δ (ppm): 2.08 (s, 3H), 2.24 (d, 3H), 3.69 (s, 3H), 3.87 (s, 3H), 5.18 (s, 2H), 6.35 (s, 1H), 7.15-7.48 (m, 8H)

Example 33

Preparation of methyl-(E)-2-[[[[[2-[4-(2-chloro-2-fluorovinyl)phenyl](1-methyl)methylidene]amino]oxy]methyl]phenyl]-2-methoxyiminoacetate The procedure of Example 1 was repeated except for using 1-(4-(2-chloro-2-fluorovinyl)phenyl)ethane-1-oneoxime (1.07 g, 5 mmol) instead of 3-(2,2-dichlorovinyl)phenol to obtain the title compound (1.78 g, 85%).
$^1$H-NMR (CDCl$_3$, TMS) δ (ppm): 2.26 (d, 3H), 3.71 (s, 3H), 3.87 (s, 3H), 5.20 (s, 2H), 6.37 (s, 1H), 7.17-7.54 (m, 8H)

Example 34

Preparation of (E)-2-[[[[[2-[4-(2-chloro-2-fluorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[4-(2-chloro-2-fluorovinyl)phenyl](1-methyl)methylidene]amino]oxy]methyl]phenyl]-2-methoxyiminoacetate (0.42 g, 1 mmol) obtained in Example 33 instead of methyl-(E)-2-(2-((3-(2,2-dichlorovinyl)phenoxy)methyl)phenyl)-2-methoxyiminoacetate to obtain the title compound (0.369 g, 88%).
$^1$H-NMR (CDCl$_3$, TMS) δ (ppm): 2.11 (s, 3H), 2.25 (d, 3H), 3.72 (s, 3H), 3.87 (s, 3H), 5.18 (s, 2H), 6.35 (s, 1H), 7.15-7.51 (m, 8H)

Example 35

Preparation of methyl-(E)-2-[[[[[2-[3-(2-bromo-2-chlorovinyl)phenyl](1-methyl)methylidene]amino]oxy]methyl]phenyl]-2-methoxyiminoacetate The procedure of Example 1 was repeated except for using 1-(3-(2-bromo-2-chlorovinyl)phenyl)ethane-1-oneoxime (1.37 g, 5 mmol) instead of 3-(2,2-dichlorovinyl)phenol to obtain the title compound (2.01 g, 84%).
$^1$H-NMR (CDCl$_3$, TMS) δ (ppm): 2.17 (d, 3H), 3.67 (s, 3H), 3.85 (s, 3H), 5.21 (s, 2H), 7.19 (s, 1H), 7.27-7.77 (m, 8H)

Example 36

Preparation of (E)-2-[[[[[2-[3-(2-bromo-2-chlorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[3-(2-bromo-2-chlorovinyl)phenyl](1-methyl)methylidene]amino]oxy]methyl]phenyl]-2-methoxyiminoacetate (0.48 g, 1 mmol) obtained in Example 35 instead of methyl-(E)-2-(2-((3-(2,2-dichlorovinyl)phenoxy)methyl)phenyl)-2-methoxyiminoacetate to obtain the title compound (0.401 g, 85%).
$^1$H-NMR (CDCl$_3$, TMS) δ (ppm): 2.15 (s, 3H), 2.26 (d, 3H), 3.69 (s, 3H), 3.87 (s, 3H), 5.27 (s, 2H), 7.21 (s, 1H), 7.28-7.78 (m, 8H)

Example 37

Preparation of methyl-(E)-2-[[[[[2-[4-(2-bromo-2-chlorovinyl)phenyl](1-methyl)methylidene]amino]oxy]methyl]phenyl]-2-methoxyiminoacetate The procedure of Example 1 was repeated except for using 1-(4-(2-bromo-2-chlorovinyl)phenyl)ethane-1-oneoxime (1.37 g, 5 mmol) instead of 3-(2,2-dichlorovinyl)phenol to obtain the title compound (2.08 g, 87%).

$^1$H-NMR (CDCl$_3$, TMS) δ (ppm): 2.20 (d, 3H), 3.67 (s, 3H), 3.85 (s, 3H), 5.21 (s, 2H), 7.19 (s, 1H), 7.25-7.80 (m, 8H)

Example 38

Preparation of (E)-2-[[[[[2-[4-(2-bromo-2-chlorovinyl)phenyl](1-methyl)methylidene]amino]oxy]methyl]phenyl]-2-methoxyimino-N-methylacetamide The procedure of Example 2 was repeated except for using methyl-(E)-2-[[[[[2-[4-(2-bromo-2-chlorovinyl)phenyl](1-methyl)methylidene]amino]oxy]methyl]phenyl]-2-methoxyiminoacetate (0.48 g, 1 mmol) obtained in Example 37 instead of methyl-(E)-2-(2-((3-(2,2-dichlorovinyl)phenoxy)methyl)phenyl)-2-methoxyiminoacetate to obtain the title compound (0.401 g, 85%).

$^1$H-NMR (CDCl$_3$, TMS) δ (ppm): 2.19 (s, 3H), 2.28 (d, 3H), 3.69 (s, 3H), 3.87 (s, 3H), 5.27 (s, 2H), 7.21 (s, 1H), 7.30-7.82 (m, 8H)

Example 39

Preparation of methyl-(E)-2-(2-((2-chloro-4-(2,2-dichlorovinyl)phenoxy)methyl)phenyl)-2-methoxyiminoacetate 2-chloro-4-(2,2-dichlorovinyl)phenol (2.23 g, 10 mmol) obtained in Preparation Example 31 was dissolved in 50 ml of acetonitrile, potassium carbonate (2.1 g, 15.2 mmol) was added thereto, and the mixture was stirred for minutes. Methyl-(2E)-2-methoxyimino-2-(2'-bromomethyl)phenylacetate (3.95 g, 10 mmol) obtained in Preparation Example 1 was added to the reaction mixture and the mixture was refluxed for 5 hours. After completion of the reaction, unreacted solid was filtered to remove therefrom, and the filtrate was distilled under a reduced pressure. The resulting residue was subjected to column chromatography (ethyl acetate:n-hexane=1:4) to obtain the title compound (3.68 g, 86%).

$^1$H-NMR (CDCl$_3$, TMS) δ (ppm): 3.86 (s, 3H), 4.03 (s, 3H), 5.04 (s, 2H), 6.71 (s, 1H), 6.83-7.61 (m, 7H)
MS: 427.0

Example 40

Preparation of (E)-2-(2-((2-chloro-4-(2,2-dichlorovinyl)phenoxy)methyl)phenyl)-2-methoxyimino-N-methylacetamide Methyl-(E)-2-(2-((2-chloro-4-(2,2-dichlorovinyl)phenoxy)methyl)phenyl)-2-methoxyiminoacetate (0.428 g, 1 mmol) obtained in Example 39 was added to 10 ml of methanol. 40% methylamine solution (0.39 g, 5 mmol) was slowly added thereto, and the mixture was stirred at room temperature for 6 hours. The solvent was removed therefrom under a reduced pressure. After adding water thereto, the mixture was extracted three times with ethyl acetate. The combined organic layer was dried over anhydrous magnesium sulfate, filtered and distilled under a reduced pressure. The resulting residue was subjected to column chromatography (ethyl acetate:n-hexane=1:4) to obtain the title compound (0.38 g, 89%).

$^1$H-NMR (CDCl$_3$, TMS) δ (ppm): 2.89 (d, 3H), 3.93 (s, 3H), 5.07 (s, 2H), 6.70 (s, 1H), 6.76 (s, 1H), 6.78-7.61 (m, 7H)
MS: 426.0

Example 41

Preparation of methyl-(E)-2-(2-((4-(2,2-dichlorovinyl)-2-methylphenoxy)methyl)phenyl)-2-methoxyiminoacetate The procedure of Example 39 was repeated except for using 4-(2,2-dichlorovinyl)-2-methylphenol (1.54 g, 7.6 mmol) instead of 2-chloro-4-(2,2-dichlorovinyl)phenol to obtain the title compound (2.82 g, 91%).

$^1$H-NMR (CDCl$_3$, TMS) δ (ppm): 2.24 (s, 3H), 3.82 (s, 3H), 4.02 (s, 3H), 4.98 (s, 2H), 6.74 (s, 1H), 6.77-7.56 (m, 7H)
MS: 407.1

Example 42

Preparation of (E)-2-(2-((4-(2,2-dichlorovinyl)-2-methylphenoxy)methyl)phenyl)-2-methoxyimino-N-methylacetamide The procedure of Example 40 was repeated except for using methyl-(E)-2-(2-((4-(2,2-dichlorovinyl)-2-methylphenoxy)methyl)phenyl)-2-methoxyiminoacetate (0.408 g, 1 mmol) obtained in Example 41 instead methyl-(E)-2-(2-((2-chloro-4-(2,2-dichlorovinyl)phenoxy)methyl)phenyl)-2-methoxyiminoacetate to obtain the title compound (0.350 g, 86%).

$^1$H-NMR (CDCl$_3$, TMS) δ (ppm): 2.23 (s, 3H), 2.88 (d, 3H), 3.94 (s, 3H), 4.98 (s, 2H), 6.73 (s, 1H), 6.71-6.79 (m, 2H), 7.20-7.54 (m, 6H)
MS: 406.0

Example 43

Preparation of methyl-(E)-2-(2-((2-chloro-3-(2,2-dichlorovinyl)phenoxy)methyl)phenyl)-2-methoxyiminoacetate The procedure of Example 39 was repeated except for using 2-chloro-3-(2,2-dichlorovinyl)phenol (1.65 g, 7.4 mmol) instead of 2-chloro-4-(2,2-dichlorovinyl)phenol to obtain the title compound (2.76 g, 87%).

$^1$H-NMR (CDCl$_3$, TMS) δ (ppm): 3.85 (s, 3H), 4.03 (s, 3H), 5.02 (s, 2H), 6.83 (d, 1H), 7.05 (s, 1H), 7.13-7.61 (m, 6H)
MS: 427.0

Example 44

Preparation of (E)-2-(2-((2-chloro-3-(2,2-dichlorovinyl)phenoxy)methyl)phenyl)-2-methoxyimino-N-methylacetamide The procedure of Example 40 was repeated except for using methyl-(E)-2-(2-((2-chloro-3-(2,2-dichlorovinyl)phenoxy)methyl)phenyl)-2-methoxyiminoacetate (0.429 g, 1 mmol) obtained in Example 43 instead of methyl-(E)-2-(2-

((2-chloro-4-(2,2-dichlorovinyl)phenoxy)methyl)phenyl)-2-methoxyiminoacetate to obtain the title compound (0.376 g, 88%).

$^1$H-NMR (CDCl$_3$, TMS) δ (ppm): 2.88 (d, 3H), 3.96 (s, 3H), 5.06 (s, 2H), 6.74 (s, 1H), 6.84-6.88 (m, 1H), 7.05 (s, 1H), 7.13-7.45 (m, 6H)
MS: 426.0

Example 45

Preparation of methyl-(E)-2-(2-((2-(2,2-dichlorovinyl)-4-methylphenoxy)methyl)phenyl)-2-methoxyiminoacetate The procedure of Example 39 was repeated except for using 2-(2,2-dichlorovinyl)-4-methylphenol (2.03 g, 10 mmol) instead of 2-chloro-4-(2,2-dichlorovinyl)phenol to obtain the title compound (3.80 g, 93%).

$^1$H-NMR (CDCl$_3$, TMS) δ (ppm): 2.28 (s, 3H), 3.89 (s, 3H), 4.03 (s, 3H), 5.01 (s, 2H), 6.70 (s, 1H), 6.84-7.61 (m, 8H)
MS: 407.1

Example 46

Preparation of (E)-2-(2-((2-(2,2-dichlorovinyl)-4-methylphenoxy)methyl)phenyl)-2-methoxyimino-N-methylacetamide The procedure of Example 40 was repeated except for using methyl-(E)-2-(2-((2-(2,2-dichlorovinyl)-4-methylphenoxy)methyl)phenyl)-2-methoxyiminoacetate (0.48 g, 1 mmol) obtained in Example 45 instead of methyl-(E)-2-(2-((2-chloro-4-(2,2-dichlorovinyl)phenoxy)methyl)phenyl)-2-methoxyiminoacetate to obtain the title compound (0.388 g, 95%).

$^1$H-NMR (CDCl$_3$, TMS) δ (ppm): 2.28 (s, 3H), 2.87 (d, 3H), 3.92 (s, 3H), 4.97 (s, 2H), 6.71-6.74 (m, 2H), 7.07 (s, 1H), 7.00-7.56 (m, 6H)
MS: 406.1

Example 47

Preparation of methyl-(E)-2-(2-((5-(2,2-dichlorovinyl)-2-methoxyphenoxy)methyl)phenyl)-2-methoxyiminoacetate The procedure of Example 39 was repeated except for using 5-(2,2-dichlorovinyl)-2-methoxyphenol (1.75 g, 8 mmol) instead of 2-chloro-4-(2,2-dichlorovinyl)phenol to obtain the title compound (2.58 g, 76%).

$^1$H-NMR (CDCl$_3$, TMS) δ (ppm): 3.85 (s, 3H), 3.88 (s, 3H), 4.05 (s, 3H), 5.01 (s, 2H), 6.69 (s, 1H), 6.84-7.57 (m, 7H)
MS: 423.1

Example 48

Preparation of (E)-2-(2-((5-(2,2-dichlorovinyl)-2-methoxyphenoxy)methyl)phenyl)-2-methoxyimino-N-methylacetamide The procedure of Example 40 was repeated except for using methyl-(E)-2-(2-((5-(2,2-dichlorovinyl)-2-methoxyphenoxy)methyl)phenyl)-2-methoxyiminoacetate (0.424 g, 1 mmol) obtained in Example 47 instead of methyl-(E)-2-(2-((2-chloro-4-(2,2-dichlorovinyl)phenoxy)methyl)phenyl)-2-methoxyiminoacetate to obtain the title compound (0.351 g, 83%).

$^1$H-NMR (CDCl$_3$, TMS) δ (ppm): 2.90 (d, 3H), 3.88 (s, 3H), 3.95 (s, 3H), 5.02 (s, 2H), 6.72 (s, 1H), 6.75-7.55 (m, 8H)
MS: 422.0

Example 49

Preparation of methyl-(E)-2-(2-((2-(2,2-dichlorovinyl)-6-methylphenoxy)methyl)phenyl)-2-methoxyiminoacetate The procedure of Example 39 was repeated except for using 2-(2,2-dichlorovinyl)-6-methylphenol (2.03 g, 10 mmol) instead of 2-chloro-4-(2,2-dichlorovinyl)phenol to obtain the title compound (3.18 g, 78%).

$^1$H-NMR (CDCl$_3$, TMS) δ (ppm): 2.21 (s, 3H), 3.83 (s, 3H), 4.03 (s, 3H), 4.66 (s, 2H), 6.41 (s, 1H), 7.00 (s, 1H), 7.03-7.66 (m, 7H)
MS: 407.0

Example 50

Preparation of (E)-2-(2-((2-(2,2-dichlorovinyl)-6-methylphenoxy)methyl)phenyl)-2-methoxyimino-N-methylacetamide The procedure of Example 40 was repeated except for using methyl-(E)-2-(2-((2-(2,2-dichlorovinyl)-6-methylphenoxy)methyl)phenyl)-2-methoxyiminoacetate (0.408 g, 1 mmol) obtained in Example 49 instead of methyl-(E)-2-(2-((2-chloro-4-(2,2-dichlorovinyl)phenoxy)methyl)phenyl)-2-methoxyiminoacetate to obtain the title compound (0.362 g, 89%).

$^1$H-NMR (CDCl$_3$, TMS) δ (ppm): 2.23 (s, 3H), 2.90 (d, 3H), 3.95 (s, 3H), 4.66 (s, 2H), 6.77 (s, 1H), 7.02 (s, 1H), 7.05-7.67 (m, 7H)
MS: 406.9

Example 51

Preparation of methyl-(E)-2-(2-((2-bromo-3-(2,2-dichlorovinyl)-6-methoxyphenoxy)methyl)phenyl)-2-methoxyiminoacetate The procedure of Example 39 was repeated except for using 2-bromo-3-(2,2-dichlorovinyl)-6-methoxyphenol (1.79 g, 6 mmol) instead of 2-chloro-4-(2,2-dichlorovinyl)phenol to obtain the title compound (2.44 g, 81%).

$^1$H-NMR (CDCl$_3$, TMS) δ (ppm): 3.84 (s, 3H), 3.86 (s, 3H), 4.02 (s, 3H), 4.83 (s, 2H), 6.90 (s, 1H), 6.87-7.88 (m, 6H)
MS: 500.8

Example 52

Preparation of (E)-2-(2-((2-(2-bromo-3-(2,2-dichlorovinyl)-6-phenoxy)methyl)phenyl)-2-methoxyimino-N-methylacetamide The procedure of Example 40 was repeated except for using methyl-(E)-2-(2-((2-bromo-3-(2,2-dichlorovinyl)-6-methoxyphenoxy)methyl)phenyl)-2-methoxyiminoacetate (0.503 g, 1 mmol) obtained in Example 51 instead of methyl-(E)-2-(2-((2-chloro-4-(2,2-dichlorovinyl)phenoxy)methyl)phenyl)-2-methoxyiminoacetate to obtain the title compound (0.412 g, 82%).

$^1$H-NMR (CDCl$_3$, TMS) δ (ppm): 2.89 (d, 3H), 3.83 (s, 3H), 3.94 (s, 3H), 4.85 (s, 2H), 6.67 (s, 1H), 6.90 (s, 1H), 6.87-7.82 (m, 6H)
MS: 499.9

Example 53

Preparation of methyl-(E)-2-(2-((2-bromo-4-(2,2-dichlorovinyl)phenoxy)methyl)phenyl)-2-methoxyiminoacetate The procedure of Example 39 was repeated except for using 2-bromo-4-(2,2-dichlorovinyl)phenol (1.34 g, 5 mmol) instead of 2-chloro-4-(2,2-dichlorovinyl)phenol to obtain the title compound (1.84 g, 78%).

$^1$H-NMR (CDCl$_3$, TMS) δ (ppm): 3.87 (s, 3H), 4.04 (s, 3H), 5.04 (s, 2H), 6.71 (s, 1H), 6.80-7.77 (m, 7H)
MS: 472.9

Example 54

Preparation of (E)-2-(2-((2-bromo-4-(2,2-dichlorovinyl)phenoxy)methyl)phenyl)-2-methoxyimino-N-methylacetamide The procedure of Example 40 was repeated except for using methyl-(E)-2-(2-((2-bromo-4-(2,2-dichlorovinyl)phenoxy)methyl)phenyl)-2-methoxyiminoacetate (0.473 g, 1 mmol) obtained in Example 53 instead of methyl-(E)-2-(2-((2-chloro-4-(2,2-dichlorovinyl)phenoxy)methyl)phenyl)-2-methoxyiminoacetate to obtain the title compound (0.430 g, 91%).

$^1$H-NMR (CDCl$_3$, TMS) δ (ppm): 2.90 (d, 3H), 3.94 (s, 3H), 5.07 (s, 2H), 6.70 (s. 1H), 6.77-7.77 (m, 8H)
MS: 471.8

Example 55

Preparation of methyl-(E)-2-(2-((2-(2,2-dichlorovinyl)-4-fluorophenoxy)methyl)phenyl)-2-methoxyiminoacetate The procedure of Example 39 was repeated except for using 2-(2,2-dichlorovinyl)-4-fluorophenol (1.45 g, 7.0 mmol) instead of 2-chloro-4-(2,2-dichlorovinyl)phenol to obtain the title compound (2.68 g, 93%).

$^1$H-NMR (CDCl$_3$, TMS) δ (ppm): 3.84 (s, 3H), 4.22 (s, 3H), 5.04 (s, 2H), 6.92 (d, 1H), 7.05 (s, 1H), 7.17-7.63 (m, 6H)
MS: 411.0

Example 56

Preparation of (E)-2-(2-((2-(2,2-dichlorovinyl)-4-fluorophenoxy)methyl)phenyl)-2-methoxyimino-N-methylacetamide The procedure of Example 40 was repeated except for using methyl-(E)-2-(2-((2-(2,2-dichlorovinyl)-4-fluorophenoxy)methyl)phenyl)-2-methoxyiminoacetate (0.41 g, 1 mmol) obtained in Example 55 instead of methyl-(E)-2-(2-((2-chloro-4-(2,2-dichlorovinyl)phenoxy)methyl)phenyl)-2-methoxyiminoacetate to obtain the title compound (0.358 g, 87%).

$^1$H-NMR (CDCl$_3$, TMS) δ (ppm): 2.88 (d, 3H), 3.96 (s, 3H), 5.06 (s, 2H), 6.74 (s, 1H), 6.84-6.88 (m, 1H), 7.05 (s, 1H), 7.13-7.45 (m, 6H)
MS: 410.0

Example 57

Preparation of methyl-(E)-2-(2-((3-chloro-4-(2,2-dichlorovinyl)phenoxy)methyl)phenyl)-2-methoxyiminoacetate The procedure of Example 39 was repeated except for using 3-chloro-4-(2,2-dichlorovinyl)phenol (1.61 g, 7.2 mmol) instead of 2-chloro-4-(2,2-dichlorovinyl)phenol to obtain the title compound (2.65 g, 86%).

$^1$H-NMR (CDCl$_3$, TMS) δ (ppm): 3.89 (s, 3H), 4.11 (s, 3H), 5.04 (s, 2H), 6.89 (d, 1H), 7.07 (s, 1H), 7.12-7.66 (m, 6H)
MS: 427.0

Example 58

Preparation of (E)-2-(2-((3-chloro-4-(2,2-dichlorovinyl)phenoxy)methyl)phenyl)-2-methoxyimino-N-methylacetamide The procedure of Example 40 was repeated except for using methyl-(E)-2-(2-((3-chloro-4-(2,2-dichlorovinyl)phenoxy)methyl)phenyl)-2-methoxyiminoacetate (0.428 g, 1 mmol) obtained in Example 57 instead of methyl-(E)-2-(2-((2-chloro-4-(2,2-dichlorovinyl)phenoxy)methyl)phenyl)-2-methoxyiminoacetate to obtain the title compound (0.389 g, 91%).

$^1$H-NMR (CDCl$_3$, TMS) δ (ppm): 2.91 (d, 3H), 3.99 (s, 3H), 5.08 (s, 2H), 6.82 (s, 1H), 6.83-6.88 (m, 1H), 7.04 (s, 1H), 7.21-7.50 (m, 6H)
MS: 426.0

Example 59

Preparation of methyl-(E)-2-(2-((4-(2,2-dichlorovinyl)-2-ethoxyphenoxy)methyl)phenyl)-2-methoxyiminoacetate The procedure of Example 39 was repeated except for using 4-(2,2-dichlorovinyl)-2-ethoxyphenol (2.33 g, 10 mmol) instead of 2-chloro-4-(2,2-dichlorovinyl)phenol to obtain the title compound (4.08 g, 93%).

$^1$H-NMR (CDCl$_3$, TMS) δ (ppm): 1.33 (t, 3H), 3.88 (s, 3H), 3.98 (m, 2H), 4.00 (s, 3H), 5.02 (s, 2H), 6.62-7.44 (m, 8H)
MS: 437.0

Example 60

Preparation of (E)-2-(2-((4-(2,2-dichlorovinyl)-2-ethoxyphenoxy)methyl)phenyl)-2-methoxyimino-N-methylacetamide The procedure of Example 40 was repeated except for using methyl-(E)-2-(2-((4-(2,2-dichlorovinyl)-2-ethoxyphenoxy)methyl)phenyl)-2-methoxyiminoacetate (0.438 g, 1 mmol) obtained in Example 59 instead of methyl-(E)-2-(2-((2-chloro-4-(2,2-dichlorovinyl)phenoxy)methyl)phenyl)-2-methoxyiminoacetate to obtain the title compound (0.407 g, 93%).

$^1$H-NMR (CDCl$_3$, TMS) δ (ppm): 1.33 (t, 3H), 2.74 (s, 3H), 3.98 (m, 2H), 4.00 (s, 3H), 5.02 (s, 2H), 6.62-7.44 (m, 8H)
MS: 436.1

Example 61

Preparation of methyl-(E)-2-(2-((5-bromo-2-(2,2-dichlorovinyl)phenoxy)methyl)phenyl)-2-methoxyiminoacetate The procedure of Example 39 was repeated except for using 5-bromo-2-(2,2-dichlorovinyl)phenol (2.52 g, 9.4 mmol) instead of 2-chloro-4-(2,2-dichlorovinyl)phenol to obtain the title compound (3.91 g, 88%).
$^1$H-NMR (CDCl$_3$, TMS) δ (ppm): 3.90 (s, 3H), 4.09 (s, 3H), 5.11 (s, 2H), 6.72 (s, 1H), 6.88-7.71 (m, 7H)
MS: 470.9

Example 62

Preparation of (E)-2-(2-((5-bromo-2-(2,2-dichlorovinyl)phenoxy)methyl)phenyl)-2-methoxyimino-N-methylacetamide The procedure of Example 40 was repeated except for using methyl-(E)-2-(2-((5-bromo-2-(2,2-dichlorovinyl)phenoxy)methyl)phenyl)-2-methoxyiminoacetate (0.473 g, 1 mmol) obtained in Example 61 instead of methyl-(E)-2-(2-((2-chloro-4-(2,2-dichlorovinyl)phenoxy)methyl)phenyl)-2-methoxyiminoacetate to obtain the title compound (0.368 g, 78%).
$^1$H-NMR (CDCl$_3$, TMS) δ (ppm): 2.91 (d, 3H), 4.08 (s, 3H), 5.02 (s, 2H), 6.70-7.53 (m, 9H)
MS: 469.9

Example 63

Preparation of methyl-(E)-2-(2-((4-(2,2-dibromovinyl)-2-chlorophenoxy)methyl)phenyl)-2-methoxyiminoacetate The procedure of Example 39 was repeated except for using 4-(2,2-dibromovinyl)-2-chlorophenol (2.84 g, 9.1 mmol) instead of 2-chloro-4-(2,2-dichlorovinyl)phenol to obtain the title compound (4.10 g, 87%).
$^1$H-NMR (CDCl$_3$, TMS) δ (ppm): 3.88 (s, 3H), 4.05 (s, 3H), 5.07 (s, 2H), 6.69 (s, 1H), 6.90-7.61 (m, 7H)
MS: 514.9

Example 64

Preparation of (E)-2-(2-((4-(2,2-dibromovinyl)-2-chlorophenoxy)methyl)phenyl)-2-methoxyimino-N-methylacetamide The procedure of Example 40 was repeated except for using methyl-(E)-2-(2-((4-(2,2-dibromovinyl)-2-chlorophenoxy)methyl)phenyl)-2-methoxyiminoacetate (0.518 g, 1 mmol) obtained in Example 63 instead of methyl-(E)-2-(2-((2-chloro-4-(2,2-dichlorovinyl)phenoxy)methyl)phenyl)-2-methoxyiminoacetate to obtain the title compound (0.413 g, 80%).
$^1$H-NMR (CDCl$_3$, TMS) δ (ppm): 2.92 (d, 3H), 3.87 (s, 3H), 3.96 (s, 3H), 5.07 (s, 2H), 6.74-7.60 (m, 9H)
MS: 513.7

Example 65

Preparation of methyl-(E)-2-(2-((4-(2,2-dibromovinyl)-2-methylphenoxy)methyl)phenyl)-2-methoxyiminoacetate The procedure of Example 39 was repeated except for using 4-(2,2-dibromovinyl)-2-methylphenol (1.87 g, 6.4 mmol) instead of 2-chloro-4-(2,2-dichlorovinyl)phenol to obtain the title compound (2.90 g, 91%).
$^1$H-NMR (CDCl$_3$, TMS) δ (ppm): 2.25 (s, 3H), 3.81 (s, 3H), 4.00 (s, 3H), 5.04 (s, 2H), 6.77 (s, 1H), 6.79-7.66 (m, 7H)
MS: 494.9

Example 66

Preparation of (E)-2-(2-((4-(2,2-dibromovinyl)-2-methylphenoxy)methyl)phenyl)-2-methoxyimino-N-methylacetamide The procedure of Example 40 was repeated except for using 2-(2-((4-(2,2-dibromovinyl)-2-methylphenoxy)methyl)phenyl)-2-methoxyiminoacetate (0.97 g, 1 mmol) obtained in Example 65 instead of methyl-(E)-2-(2-((2-chloro-4-(2,2-dichlorovinyl)phenoxy)methyl)phenyl)-2-methoxyiminoacetate to obtain the title compound (0.408 g, 82%).
$^1$H-NMR (CDCl$_3$, TMS) δ (ppm): 2.31 (s, 3H), 2.92 (d, 3H), 3.98 (s, 3H), 5.01 (s, 2H), 6.70 (s, 1H), 6.72-6.79 (m, 2H), 7.33-7.68 (m, 6H)
MS: 493.9

Example 67

Preparation of methyl-(E)-2-(2-((3-(2,2-dibromovinyl)-2-chlorophenoxy)methyl)phenyl)-2-methoxyiminoacetate The procedure of Example 39 was repeated except for using 3-(2,2-dibromovinyl)-2-chlorophenol (1.87 g, 6 mmol) instead of 2-chloro-4-(2,2-dichlorovinyl)phenol to obtain the title compound (2.36 g, 76%).
$^1$H-NMR (CDCl$_3$, TMS) δ (ppm): 3.84 (s, 3H), 4.02 (s, 3H), 5.09 (s, 2H), 6.83 (d, 1H), 7.11 (s, 1H), 7.34-7.62 (m, 6H)
MS: 514.9

Example 68

Preparation of (E)-2-(2-((3-(2,2-dibromovinyl)-2-chlorophenoxy)methyl)phenyl)-2-methoxyimino-N-methylacetamide The procedure of Example 40 was repeated except for using methyl-(E)-2-(2-((3-(2,2-dibromovinyl)-2-chlorophenoxy)methyl)phenyl)-2-methoxyiminoacetate (0.517 g, 1 mmol) obtained in Example 67 instead of methyl-(E)-2-(2-((2-chloro-4-(2,2-dichlorovinyl)phenoxy)methyl)phenyl)-2-methoxyiminoacetate to obtain the title compound (0.434 g, 84%).
$^1$H-NMR (CDCl$_3$, TMS) δ (ppm): 2.86 (d, 3H), 3.92 (s, 3H), 5.07 (s, 2H), 6.74 (s, 1H), 6.82-6.89 (m, 1H), 7.06 (s, 1H), 7.25-7.55 (m, 6H)
MS: 513.9

Example 69

Preparation of methyl-(E)-2-(2-((2-(2,2-dibromovinyl)-4-methylphenoxy)methyl)phenyl)-2-methoxyiminoacetate The procedure of Example 39 was repeated except for using 2-(2,2-dibromovinyl)-4-methylphenol (1.81 g, 6.2 mmol) instead of 2-chloro-4-(2,2-dichlorovinyl)phenol to obtain the title compound (2.87 g, 93%).
$^1$H-NMR (CDCl$_3$, TMS) δ (ppm): 3.84 (s, 3H), 3.89 (s, 3H), 4.02 (s, 3H), 5.04 (s, 2H), 6.74 (s, 1H), 6.91-7.66 (m, 8H)
MS: 494.1

Example 70

Preparation of (E)-2-(2-((2-(2,2-dibromovinyl)-4-methylphenoxy)methyl)phenyl)-2-methoxyimino-N-methylacetamide The procedure of Example 40 was repeated except for using methyl-(E)-2-(2-((2-(2,2-dibromovinyl)-4-methylphenoxy)methyl)phenyl)-2-methoxyiminoacetate (0.497 g, 1 mmol) obtained in Example 69 instead of methyl-(E)-2-(2-((2-chloro-4-(2,2-dichlorovinyl)phenoxy)methyl)phenyl)-2-methoxyiminoacetate to obtain the title compound (0.452 g, 91%).

$^1$H-NMR (CDCl$_3$, TMS) δ (ppm): 2.34 (s, 3H), 2.85 (d, 3H), 3.93 (s, 3H), 4.97 (s, 2H), 6.69-6.75 (m, 2H), 7.11 (s, 1H), 7.04-7.67 (m, 6H)
MS: 493.9

Example 71

Preparation of methyl-(E)-2-(2-((5-(2,2-dibromovinyl)-2-methoxyphenoxy)methyl)phenyl)-2-methoxyiminoacetate The procedure of Example 39 was repeated except for using 5-(2,2-dibromovinyl)-2-methoxyphenol (2.22 g, 7.2 mmol) instead of 2-chloro-4-(2,2-dichlorovinyl)phenol to obtain the title compound (2.96 g, 80%).

$^1$H-NMR (CDCl$_3$, TMS) δ (ppm): 3.82 (s, 3H), 3.87 (s, 3H), 4.66 (s, 3H), 5.05 (s, 2H), 6.69 (s, 1H), 7.04-7.72 (m, 7H)
MS: 510.9

Example 72

Preparation of (E)-2-(2-((5-(2,2-dibromovinyl)-2-methoxyphenoxy)methyl)phenyl)-2-methoxyimino-N-methylacetamide The procedure of Example 40 was repeated except for using methyl-(E)-2-(2-((5-(2,2-dibromovinyl)-2-methoxyphenoxy)methyl)phenyl)-2-methoxyiminoacetate (0.513 g, 1 mmol) obtained in Example 71 instead of methyl-(E)-2-(2-((2-chloro-4-(2,2-dichlorovinyl)phenoxy)methyl)phenyl)-2-methoxyiminoacetate to obtain the title compound (0.492 g, 96%).

$^1$H-NMR (CDCl$_3$, TMS) δ (ppm): 2.88 (d, 3H), 3.86 (s, 3H), 3.97 (s, 3H), 5.11 (s, 2H), 6.78 (s, 1H), 6.97-7.55 (m, 8H)
MS: 509.9

Example 73

Preparation of methyl-(E)-2-(2-((2-(2,2-dibromovinyl)-6-methylphenoxy)methyl)phenyl)-2-methoxyiminoacetate The procedure of Example 39 was repeated except for using 2-(2,2-dibromovinyl)-6-methylphenol (2.34 g, 8 mmol) instead of 2-chloro-4-(2,2-dichlorovinyl)phenol to obtain the title compound (3.46 g, 87%).

$^1$H-NMR (CDCl$_3$, TMS) δ (ppm): 2.23 (s, 3H), 3.83 (s, 3H), 4.04 (s, 3H), 4.74 (s, 2H), 6.89 (s, 1H), 7.24-7.64 (m, 7H)
MS: 494.9

Example 74

Preparation of (E)-2-(2-((2-(2,2-dibromovinyl)-6-methylphenoxy)methyl)phenyl)-2-methoxyimino-N-methylacetamide The procedure of Example 40 was repeated except for using methyl-(E)-2-(2-((2-(2,2-dibromovinyl)-6-methylphenoxy)methyl)phenyl)-2-methoxyiminoacetate (0.497 g, 1 mmol) obtained in Example 73 instead of methyl-(E)-2-(2-((2-chloro-4-(2,2-dichlorovinyl)phenoxy)methyl)phenyl)-2-methoxyiminoacetate to obtain the title compound (0.427 g, 86%).

$^1$H-NMR (CDCl$_3$, TMS) δ (ppm): 2.31 (s, 3H), 2.92 (d, 3H), 3.95 (s, 3H), 4.64 (s, 2H), 6.89 (s, 1H), 7.09 (s, 1H), 7.14-7.62 (m, 7H)
MS: 493.9

Example 75

Preparation of methyl-(E)-2-(2-((2-bromo-3-(2,2-dibromovinyl)-6-methoxyphenoxy)methyl)phenyl)-2-methoxyiminoacetate The procedure of Example 39 was repeated except for using 2-bromo-3-(2,2-dibromovinyl)-6-methoxyphenol (2.32 g, 6 mmol) instead of 2-chloro-4-(2,2-dichlorovinyl)phenol to obtain the title compound (2.80 g, 79%).

$^1$H-NMR (CDCl$_3$, TMS) δ (ppm): 3.84 (s, 3H), 3.87 (s, 3H), 4.04 (s, 3H), 4.92 (s, 2H), 6.94 (s, 1H), 6.86-7.88 (m, 6H)
MS: 588.9

Example 76

Preparation of (E)-2-(2-((2-(2-bromo-3-(2,2-dibromovinyl)-6-methoxyphenoxy)methyl)phenyl)-2-methoxyimino-N-methylacetamide The procedure of Example 40 was repeated except for using methyl-(E)-2-(2-((2-bromo-3-(2,2-dibromovinyl)-6-methoxyphenoxy)methyl)phenyl)-2-methoxyiminoacetate (0.592 g, 1 mmol) obtained in Example 75 instead of methyl-(E)-2-(2-((2-chloro-4-(2,2-dichlorovinyl)phenoxy)methyl)phenyl)-2-methoxyiminoacetate to obtain the title compound (0.534 g, 92%).

$^1$H-NMR (CDCl$_3$, TMS) δ (ppm): 2.84 (d, 3H), 3.82 (s, 3H), 3.96 (s, 3H), 4.88 (s, 2H), 6.72 (s, 1H), 6.94 (s, 1H), 6.99-7.82 (m, 6H)
MS: 587.9

Example 77

Preparation of methyl-(E)-2-(2-((2-bromo-4-(2,2-dibromovinyl)phenoxy)methyl)phenyl)-2-methoxyiminoacetate The procedure of Example 39 was repeated except for using 2-bromo-4-(2,2-dibromovinyl)phenol (2.43 g, 6.8 mmol) instead of 2-chloro-4-(2,2-dichlorovinyl)phenol to obtain the title compound (3.21 g, 84%).

$^1$H-NMR (CDCl$_3$, TMS) δ (ppm): 3.82 (s, 3H), 4.03 (s, 3H), 5.02 (s, 2H), 6.77 (s, 1H), 6.90-7.65 (m, 7H)
MS: 558.9

Example 78

Preparation of (E)-2-(2-((2-bromo-4-(2,2-dibromovinyl)phenoxy)methyl)phenyl)-2-methoxyimino-N-methylacetamide The procedure of Example 40 was repeated except for using methyl-(E)-2-(2-((2-bromo-4-(2,2-dibromovinyl)phenoxy)methyl)phenyl)-2-methoxyiminoacetate (0.562 g, 1 mmol) obtained in Example 77 instead of methyl-(E)-2-(2-((2-chloro-4-(2,2-dichlorovinyl)phenoxy)methyl)phenyl)-2-methoxyiminoacetate to obtain the title compound (0.505 g, 90%).

$^1$H-NMR (CDCl$_3$, TMS) δ (ppm): 2.93 (d, 3H), 3.98 (s, 3H), 5.02 (s, 2H), 6.74 (s. 1H), 6.29-7.67 (m, 8H)

MS: 557.8

Example 79

Preparation of methyl-(E)-2-(2-((2-(2,2-dibromovinyl)-4-fluorophenoxy)methyl)phenyl)-2-methoxyiminoacetate The procedure of Example 39 was repeated except for using 2-(2,2-dibromovinyl)-4-fluorophenol (2.25 g, 7.6 mmol) instead of 2-chloro-4-(2,2-dichlorovinyl)phenol to obtain the title compound (3.31 g, 87%).

$^1$H-NMR (CDCl$_3$, TMS) δ (ppm): 3.83 (s, 3H), 4.23 (s, 3H), 5.06 (s, 2H), 6.98 (d, 1H), 7.02 (s, 1H), 7.19-7.76 (m, 6H)

MS: 498.9

Example 80

Preparation of (E)-2-(2-((2-(2,2-dibromovinyl)-4-fluorophenoxy)methyl)phenyl)-2-methoxyimino-N-methylacetamide The procedure of Example 40 was repeated except for using methyl-(E)-2-(2-((2-(2,2-dibromovinyl)-4-fluorophenoxy)methyl)phenyl)-2-methoxyiminoacetate (0.501 g, 1 mmol) obtained in Example 79 instead of methyl-(E)-2-(2-((2-chloro-4-(2,2-dichlorovinyl)phenoxy)methyl)phenyl)-2-methoxyiminoacetate to obtain the title compound (0.455 g, 91%).

$^1$H-NMR (CDCl$_3$, TMS) δ (ppm): 2.90 (d, 3H), 3.98 (s, 3H), 5.07 (s, 2H), 6.87 (s, 1H), 6.90-6.94 (m, 1H), 7.11 (s, 1H), 7.14-7.62 (m, 6H)

MS: 497.9

Example 81

Preparation of methyl-(E)-2-(2-((4-(2,2-dibromovinyl)-3-chlorophenoxy)methyl)phenyl)-2-methoxyiminoacetate The procedure of Example 39 was repeated except for using 4-(2,2-dibromovinyl)-3-chlorophenol (1.56 g, 5 mmol) instead of 2-chloro-4-(2,2-dichlorovinyl)phenol to obtain the title compound (1.99 g, 77%).

$^1$H-NMR (CDCl$_3$, TMS) δ (ppm): 3.90 (s, 3H), 4.08 (s, 3H), 5.07 (s, 2H), 6.92 (d, 1H), 7.11 (s, 1H), 7.14-7.72 (m, 6H)

MS: 514.9

Example 82

Preparation of (E)-2-(2-((4-(2,2-dibromovinyl)-3-chlorophenoxy)methyl)phenyl)-2-methoxyimino-N-methylacetamide The procedure of Example 40 was repeated except for using methyl-(E)-2-(2-((4-(2,2-dibromovinyl)-3-chlorophenoxy)methyl)phenyl)-2-methoxyiminoacetate (0.518 g, 1 mmol) obtained in Example 81 instead of methyl-(E)-2-(2-((2-chloro-4-(2,2-dichlorovinyl)phenoxy)methyl)phenyl)-2-methoxyiminoacetate to obtain the title compound (0.486 g, 94%).

$^1$H-NMR (CDCl$_3$, TMS) δ (ppm): 2.93 (d, 3H), 4.00 (s, 3H), 5.06 (s, 2H), 6.84 (s, 1H), 6.89-6.92 (m, 1H), 7.11 (s, 1H), 7.24-7.56 (m, 6H)

MS: 513.9

Example 83

Preparation of methyl-(E)-2-(2-((4-(2,2-dibromovinyl)-2-ethoxyphenoxy)methyl)phenyl)-2-methoxyiminoacetate The procedure of Example 39 was repeated except for using 4-(2,2-dibromovinyl)-2-ethoxyphenol (1.93 g, 6 mmol) instead of 2-chloro-4-(2,2-dichlorovinyl)phenol to obtain the title compound (2.78 g, 88%).

$^1$H-NMR (CDCl$_3$, TMS) δ (ppm): 1.42 (t, 3H), 3.90 (s, 3H), 3.99 (m, 2H), 4.04 (s, 3H), 5.01 (s, 2H), 6.89-7.53 (m, 8H)

MS: 525.0

Example 84

Preparation of (E)-2-(2-((4-(2,2-dibromovinyl)-2-ethoxyphenoxy)methyl)phenyl)-2-methoxyimino-N-methylacetamide The procedure of Example 40 was repeated except for using methyl-(E)-2-(2-((4-(2,2-dibromovinyl)-2-ethoxyphenoxy)methyl)phenyl)-2-methoxyiminoacetate (0.527 g, 1 mmol) obtained in Example 83 instead of methyl-(E)-2-(2-((2-chloro-4-(2,2-dichlorovinyl)phenoxy)methyl)phenyl)-2-methoxyiminoacetate to obtain the title compound (0.474 g, 90%).

$^1$H-NMR (CDCl$_3$, TMS) δ (ppm): 1.42 (t, 3H), 3.90 (s, 3H), 3.98 (m, 2H), 4.03 (s, 3H), 5.02 (s, 2H), 6.84-7.47 (m, 8H)

MS: 524.0

Example 85

Preparation of methyl-(E)-2-(2-((5-bromo-2-(2,2-dibromovinyl)phenoxy)methyl)phenyl)-2-methoxyiminoacetate The procedure of Example 39 was repeated except for using 5-bromo-2-(2,2-dibromovinyl)phenol (2.85 g, 8 mmol) instead of 2-chloro-4-(2,2-dichlorovinyl)phenol to obtain the title compound (2.14 g, 75%).

$^1$H-NMR (CDCl$_3$, TMS) δ (ppm): 3.92 (s, 3H), 4.11 (s, 3H), 5.10 (s, 2H), 6.78 (s, 1H), 6.90-7.72 (m, 7H)

MS: 558.9

Example 86

Preparation of (E)-2-(2-((5-bromo-2-(2,2-dibromovinyl)phenoxy)methyl)phenyl)-2-methoxyimino-N-methylacetamide The procedure of Example 40 was repeated except for using methyl-(E)-2-(2-((5-bromo-2-(2,2-dibromovinyl)phenoxy)methyl)phenyl)-2-methoxyiminoacetate (0.562 g, 1 mmol) obtained in Example 85 instead of methyl-(E)-2-(2-((2-chloro-4-(2,2-dichlorovinyl)phenoxy)methyl)phenyl)-2-methoxyiminoacetate to obtain the title compound (0.454 g, 81%).

$^1$H-NMR (CDCl$_3$, TMS) δ (ppm): 2.93 (d, 3H), 4.07 (s, 3H), 5.00 (s, 2H), 6.77-7.60 (m, 9H)
MS: 557.9

Test Example

Fungicidal Activity Test

To examine fungicidal activity of the compounds of formula (I) of the present invention obtained from Examples 1 to 86 against a plant pathogen, each of the compounds was dissolved in 10% acetone, and Tween-20 was added thereto to a concentration of 2,250 ppm (500 ppm in case of a rice). 50 ml of the resulting solution was sprayed on leaves of a host plant. The plant was kept at room temperature for 24 hours to let the solvent and water evaporate, and then, a pathogenic fungus was inoculated thereonto. This procedure was repeated twice for each test. When the results of subjecting the compounds at the 1$^{st}$ test concentration of 100 ppm was more than 90%, the compounds having a C.V. of more than 90% were subjected to the 2$^{nd}$ test at reduced concentration levels of 50, 10 and 2 ppm.

Further, this procedure was repeated by using, Azoxystrobin (Syngenta), Fenarimol (DowElanco) and Kresoxim-methyl (BASF) as a comparative drug.

The fungicidal activity of the compound of the present invention is repressed by a control value (C.V.) calculated as;

$$C.V.(\%) = \frac{L.A.\ of\ control\ group - L.A.\ of\ test\ group}{L.A.\ of\ control\ group} \times 100$$

The lesion area (L.A.) attacked by the pathogenic fungus was measured according to a method of Cho (Cho, K. Y., Search Report by Korea Research Institute of Chemical Technology (1989))".

Test Example 1

Fungicidal Activity Against Rice Blast (RCB) Disease

Pyricularia oryzae Carvara KA301 was inoculated on a rice bran agar medium (rice bran 20 g, dextrose 10 g, agar 15 g and distilled water 1 l), and cultured at 26° C. for 1 week. The surface of the medium was scratched using a rubber polishman to remove aerial mycelia, and cultured under a fluorescent light (25° C. to 28° C.) for 48 hours to form a spore. Spores were suspended in sterilized water at a concentration of 1×10$^6$ spore/ml. The spore suspension was sprayed enough to soak the leaves of a RBC disease-sensitive Nakdong rice plant having 3 or 4 leaves. The rice plant was held in a humidified dark room for 24 hours, transferred to an incubator kept at 26±2° C. and a relative humidity of more than 80% and kept for 5 days to induce RCB. L.A. on a fully grown leaf appearing underneath an uppermost leaf was measured to calculate a C.V.

Test Example 2

Fungicidal Activity Against Rice Sheath Blight (RSB) Disease

Rhizoctonia solani AG-1 was cultured on a potato dextrose agar (PDA) medium for 3 days and the agar disc was inoculated and cultured on sterilized wheat bran medium in a 1 l bottle at 27±1° C. for 7 days. A mycelial mass was ground, inoculated uniformly on soil of a pot wherein a Nakdong rice plant having 2 or 3 leaves and an height of 5 cm grew, and kept in humidity chamber (28±1° C.) for 5 days to induce RSB. L.A. on a leaf sheath was measured to calculate a C.V.

Test Example 3

Fungicidal Activity Against Cucumber Gray Mold Rot (CGM) Disease

Botrytis cinerae, which was isolated from cucumber infected thereby, was inoculated on a potato agar medium (PEC) and cultured under a 12L/12D cycle at 25° C. for 15 days to form spore. The spores were scraped, filtered through a gauze and then suspended in Potato Dextrose broth at a concentration of 1×10$^6$ spore/ml. The spore suspension was sprayed on a cucumber plant having one leaf. The cucumber plant was held in a humidified room at 20° C. for 3 days. L.A. on a leaf was measured to calculate a C.V.

Test Example 4

Fungicidal Activity Against Tomato Late Blight (TLB) Disease

Phytophthora infestans was cultured on a juice agar medium (V-8 juice 200 ml, CaCO$_3$ 4.5 g, agar 15 g and distilled water 800 ml) under a 16L/8D cycle at 20° C. for 14 days to form spore. Sterilized water was added thereto, the vessel was shaken to free zoospore sacs from the fungus mass and the zoospore sacs were collected using a four-layered gauze. The zoospore sac suspension having a concentration of 1×10$^5$ spore/ml was sprayed on a young tomato plant. The tomato plant was held in a humidified room at 20° C. for 24 hours, transferred to an incubator maintained at a temperature of 20° C. and a relative humidity of more than 80%, and cultured for 4 days to induce TLB. L.A. on the primary and secondary leaves were measured to calculate a C.V.

Test Example 5

Fungicidal Activity Against Wheat Leaf Rust (WLR) Disease

Puccinia recondita was subcultured on a wheat plant in a laboratory. 15 g of wheat seeds was sowed in a pot (diameter 6.5 cm) and cultured in a greenhouse for 7 days to obtain a wheat plant having only a primary leaf. The wheat plant was inoculated with spores by shaking thereover another plant infected thereby. The inoculated wheat plant was held in a humidified room at 20° C. for 24 hours, transferred to an incubator maintained at a temperature of 20° C. and a relative humidity of 70%, and cultured for 10 days to induce WLR. L.A. on the primary leaf was measured to calculate a C.V.

Test Example 6

Fungicidal Activity Against Barley Powdery Mildew (BPM) Disease

*Erysiphae graminis* was subcultured on a barley plant in a laboratory. 15 g of barley seeds (Barley, Dong 1) was sowed in a pot (diameter 6.5 cm) and cultured in a greenhouse (25±5° C.) for 7 days to obtain a barley plant having only a primary leaf. The barley plant was inoculated with spores by shaking thereover another plant infected by BPM. The inoculated barley plant was cultured in an incubator maintained at a temperature of 22 to 24° C. and a relative humidity of 50%, and cultured for 7 days to induce BPM. L.A. on the leaf was measured to calculate an C. V.

The compounds of the present invention having a C.V. of 100% at the $1^{st}$ test concentration of 100 ppm in Test Examples 1 to 6 were subjected to the $2^{nd}$ test at a concentration of 50 ppm. Accordingly, these compounds having a C.V. of more than 90% at the $2^{nd}$ test concentration were subjected to another series of tests at reduced concentration levels of 10 and 2 ppm. The results are shown in Table 4.

TABLE 4

| Comp. No. | Conc. (ppm) | RCB | RSB | CGM | TLB | WLR | BPM |
|---|---|---|---|---|---|---|---|
| 1 | 100 | 100 | 45 | 29 | 100 | 100 | 100 |
|  | 50 | 92 | — | — | 100 | 100 | 100 |
|  | 10 | 50 | — | — | 92 | 100 | 100 |
|  | 2 | 13 | — | — | 80 | 98 | 100 |
| 2 | 100 | 100 | 32 | 34 | 100 | 100 | 100 |
|  | 50 | 100 | — | — | 100 | 98 | 100 |
|  | 10 | 97 | — | — | 100 | 90 | 100 |
|  | 2 | 90 | — | — | 98 | 30 | 100 |
| 3 | 100 | 100 | 60 | 50 | 98 | 100 | 95 |
|  | 50 | 100 | — | — | 95 | 100 | 95 |
|  | 10 | 90 | — | — | 35 | 90 | 50 |
|  | 2 | 30 | — | — | 0 | 40 | 20 |
| 4 | 100 | 100 | 100 | 75 | 100 | 100 | 100 |
|  | 50 | 100 | 100 | — | 100 | 100 | 100 |
|  | 10 | 100 | 98 | — | 100 | 100 | 100 |
|  | 2 | 100 | 90 | — | 100 | 100 | 100 |
| 5 | 100 | 100 | 32 | 34 | 93 | 92 | 87 |
|  | 50 | 100 | — | — | 55 | — | — |
|  | 10 | 97 | — | — | — | — | — |
|  | 2 | 90 | — | — | — | — | — |
| 6 | 100 | 100 | 100 | 60 | 50 | 98 | 97 |
|  | 50 | 100 | 100 | — | — | 95 | 90 |
|  | 10 | 100 | 90 | — | — | 35 | 30 |
|  | 2 | 98 | 30 | — | — | 0 | 0 |
| 7 | 100 | 100 | 100 | 35 | 100 | 100 | 100 |
|  | 50 | 100 | 100 | — | 100 | 100 | 100 |
|  | 10 | 100 | 100 | — | 100 | 100 | 100 |
|  | 2 | 100 | 98 | — | 100 | 100 | 100 |
| 8 | 100 | 100 | 32 | 7 | 100 | 100 | 100 |
|  | 50 | 100 | — | — | 100 | 98 | 100 |
|  | 10 | 97 | — | — | 100 | 90 | 100 |
|  | 2 | 90 | — | — | 98 | 90 | 99 |
| 9 | 100 | 100 | 10 | 50 | 100 | 100 | 100 |
|  | 50 | 100 | — | — | 100 | 100 | 93 |
|  | 10 | 100 | — | — | 100 | 100 | 60 |
|  | 2 | 100 | — | — | 100 | 100 | 15 |
| 10 | 100 | 100 | 45 | 50 | 100 | 100 | 98 |
|  | 50 | 100 | — | — | 100 | 100 | 60 |
|  | 10 | 100 | — | — | 100 | 100 | — |
|  | 2 | 100 | — | — | 100 | 100 | — |
| 11 | 100 | 95 | 30 | 43 | 60 | 100 | 90 |
|  | 50 | 70 | — | — | — | 90 | 60 |
|  | 10 | — | — | — | — | 40 | — |
|  | 2 | — | — | — | — | — | — |
| 12 | 100 | 97 | 15 | 40 | 93 | 82 | 80 |
|  | 50 | 90 | — | — | 55 | — | — |
|  | 10 | — | — | — | — | — | — |
|  | 2 | — | — | — | — | — | — |
| 13 | 100 | 95 | 67 | 0 | 60 | 90 | 75 |
|  | 50 | 70 | — | — | — | 40 | — |
|  | 10 | — | — | — | — | — | — |
|  | 2 | — | — | — | — | — | — |
| 14 | 100 | 95 | 15 | 40 | 98 | 72 | 60 |
|  | 50 | 90 | — | — | 35 | — | — |
|  | 10 | — | — | — | — | — | — |
|  | 2 | — | — | — | — | — | — |
| 15 | 100 | 100 | 10 | 50 | 100 | 100 | 95 |
|  | 50 | 100 | — | — | 90 | 100 | 93 |
|  | 10 | 100 | — | — | 10 | 100 | 60 |
|  | 2 | 70 | — | — | — | 100 | 15 |
| 16 | 100 | 100 | 100 | 65 | 100 | 100 | 100 |
|  | 50 | 100 | 100 | — | 100 | 100 | 100 |
|  | 10 | 100 | 98 | — | 95 | 100 | 100 |
|  | 2 | 100 | 95 | — | 93 | 100 | 100 |
| 17 | 100 | 100 | 90 | 50 | 100 | 100 | 95 |
|  | 50 | 100 | — | — | 90 | 100 | 93 |
|  | 10 | 100 | — | — | 10 | 100 | 90 |
|  | 2 | 70 | — | — | — | 100 | 35 |
| 18 | 100 | 100 | 100 | 45 | 100 | 100 | 100 |
|  | 50 | 100 | 100 | — | 100 | 100 | 100 |
|  | 10 | 100 | 98 | — | 80 | 100 | 98 |
|  | 2 | 100 | 90 | — | 30 | 100 | 95 |
| 19 | 100 | 100 | 80 | 59 | 100 | 100 | 100 |
|  | 50 | 100 | — | — | 100 | 100 | 100 |
|  | 10 | 100 | — | — | 92 | 100 | 100 |
|  | 2 | 98 | — | — | 80 | 98 | 100 |
| 20 | 100 | 100 | 75 | 74 | 100 | 100 | 100 |
|  | 50 | 100 | — | — | 100 | 98 | 100 |
|  | 10 | 97 | — | — | 100 | 90 | 100 |
|  | 2 | 90 | — | — | 98 | 30 | 100 |
| 21 | 100 | 100 | 60 | 50 | 98 | 100 | 95 |
|  | 50 | 100 | — | — | 95 | 100 | 95 |
|  | 10 | 90 | — | — | 35 | 90 | 50 |
|  | 2 | 30 | — | — | 0 | 40 | 20 |
| 22 | 100 | 100 | 100 | 45 | 100 | 100 | 100 |
|  | 50 | 100 | 100 | — | 100 | 100 | 100 |
|  | 10 | 100 | 98 | — | 100 | 100 | 100 |
|  | 2 | 100 | 90 | — | 90 | 100 | 98 |
| 23 | 100 | 100 | 100 | 34 | 93 | 80 | 95 |
|  | 50 | 100 | 100 | — | 55 | — | 80 |
|  | 10 | 97 | 100 | — | — | — | 50 |
|  | 2 | 90 | 98 | — | — | — | 20 |
| 24 | 100 | 100 | 100 | 60 | 50 | 98 | 100 |
|  | 50 | 100 | 100 | — | — | 95 | 90 |
|  | 10 | 100 | 90 | — | — | 35 | 60 |
|  | 2 | 98 | 30 | — | — | 0 | 10 |
| 25 | 100 | 100 | 100 | 35 | 100 | 100 | 100 |
|  | 50 | 100 | 100 | — | 100 | 100 | 100 |
|  | 10 | 100 | 98 | — | 100 | 100 | 100 |
|  | 2 | 100 | 90 | — | 93 | 100 | 100 |
| 26 | 100 | 100 | 32 | 7 | 100 | 100 | 100 |
|  | 50 | 100 | — | — | 100 | 98 | 100 |
|  | 10 | 97 | — | — | 100 | 90 | 100 |
|  | 2 | 90 | — | — | 98 | 90 | 99 |
| 27 | 100 | 100 | 0 | 55 | 100 | 100 | 100 |
|  | 50 | 100 | — | — | 100 | 100 | 100 |
|  | 10 | 97 | — | — | 100 | 100 | 100 |
|  | 2 | 90 | — | — | 98 | 100 | 98 |
| 28 | 100 | 95 | 35 | 50 | 60 | 100 | 90 |
|  | 50 | 70 | — | — | — | 100 | 60 |
|  | 10 | — | — | — | — | 90 | — |
|  | 2 | — | — | — | — | 40 | — |
| 29 | 100 | 100 | 30 | 24 | 100 | 100 | 100 |
|  | 50 | 100 | — | — | 100 | 100 | 93 |
|  | 10 | 100 | — | — | 100 | 100 | 60 |
|  | 2 | 100 | — | — | 100 | 100 | 15 |
| 30 | 100 | 100 | 45 | 60 | 100 | 100 | 98 |
|  | 50 | 100 | — | — | 100 | 100 | 60 |
|  | 10 | 100 | — | — | 100 | 100 | — |
|  | 2 | 100 | — | — | 100 | 90 | — |

TABLE 4-continued

| Comp. No. | Conc. (ppm) | RCB | RSB | CGM | TLB | WLR | BPM |
|---|---|---|---|---|---|---|---|
| 31 | 100 | 95 | 30 | 43 | 60 | 100 | 90 |
|  | 50 | 70 | — | — | — | 90 | 60 |
|  | 10 | — | — | — | — | 40 | — |
|  | 2 | — | — | — | — | — | — |
| 32 | 100 | 97 | 65 | 34 | 93 | 82 | 80 |
|  | 50 | 90 | — | — | 55 | — | — |
|  | 10 | — | — | — | — | — | — |
|  | 2 | — | — | — | — | — | — |
| 33 | 100 | 95 | 67 | 15 | 60 | 90 | 80 |
|  | 50 | 70 | — | — | — | 40 | — |
|  | 10 | — | — | — | — | — | — |
|  | 2 | — | — | — | — | — | — |
| 34 | 100 | 95 | 15 | 40 | 98 | 72 | 60 |
|  | 50 | 90 | — | — | 35 | — | — |
|  | 10 | — | — | — | — | — | — |
|  | 2 | — | — | — | — | — | — |
| 35 | 100 | 100 | 10 | 50 | 100 | 100 | 95 |
|  | 50 | 100 | — | — | 90 | 100 | 93 |
|  | 10 | 100 | — | — | 10 | 100 | 60 |
|  | 2 | 70 | — | — | — | 100 | 15 |
| 36 | 100 | 100 | 100 | 65 | 100 | 100 | 100 |
|  | 50 | 100 | 98 | — | 100 | 100 | 100 |
|  | 10 | 100 | 90 | — | 80 | 100 | 100 |
|  | 2 | 100 | 67 | — | 30 | 100 | 100 |
| 37 | 100 | 100 | 90 | 50 | 100 | 100 | 95 |
|  | 50 | 100 | — | — | 90 | 100 | 93 |
|  | 10 | 90 | — | — | 10 | 100 | 90 |
|  | 2 | 75 | — | — | — | 100 | 35 |
| 38 | 100 | 100 | 100 | 65 | 100 | 100 | 100 |
|  | 50 | 100 | 98 | — | 100 | 100 | 100 |
|  | 10 | 100 | 95 | — | 80 | 100 | 98 |
|  | 2 | 100 | 80 | — | 30 | 100 | 95 |
| 39 | 100 | 100 | 100 | 75 | 100 | 100 | 100 |
|  | 50 | 100 | 100 | — | 100 | 100 | 100 |
|  | 10 | 100 | 100 | — | 100 | 100 | 100 |
|  | 2 | 100 | 100 | — | 100 | 100 | 100 |
| 40 | 100 | 100 | 100 | 10 | 30 | 100 | 100 |
|  | 50 | 100 | 100 | — | — | 100 | 100 |
|  | 10 | 100 | 100 | — | — | 100 | 100 |
|  | 2 | 100 | 100 | — | — | 100 | 100 |
| 41 | 100 | 100 | 100 | 90 | 100 | 100 | 100 |
|  | 50 | 100 | 100 | 75 | 100 | 100 | 100 |
|  | 10 | 100 | 100 | — | 100 | 100 | 100 |
|  | 2 | 100 | 100 | — | 100 | 100 | 100 |
| 42 | 100 | 100 | 100 | 100 | 95 | 100 | 100 |
|  | 50 | 100 | 100 | — | 70 | 100 | 100 |
|  | 10 | 100 | 100 | — | — | 100 | 100 |
|  | 2 | 100 | 100 | — | — | 100 | 100 |
| 43 | 100 | 100 | 100 | 0 | 100 | 100 | 100 |
|  | 50 | 100 | 100 | — | 100 | 100 | 100 |
|  | 10 | 99 | 100 | — | 100 | 100 | 100 |
|  | 2 | 90 | 90 | — | 100 | 100 | 100 |
| 44 | 100 | 100 | 100 | 10 | 100 | 100 | 100 |
|  | 50 | 100 | 100 | — | 100 | 100 | 100 |
|  | 10 | 100 | 100 | — | 100 | 100 | 100 |
|  | 2 | 100 | 90 | — | 95 | 100 | 100 |
| 45 | 100 | 100 | 100 | 35 | 100 | 100 | 100 |
|  | 50 | 100 | 100 | — | 100 | 100 | 100 |
|  | 10 | 100 | 100 | — | 98 | 100 | 100 |
|  | 2 | 100 | 100 | — | 92 | 100 | 100 |
| 46 | 100 | 100 | 100 | 30 | 100 | 100 | 100 |
|  | 50 | 100 | 100 | — | 100 | 100 | 100 |
|  | 10 | 100 | 100 | — | 100 | 100 | 100 |
|  | 2 | 95 | 98 | — | 96 | 100 | 100 |
| 47 | 100 | 100 | 100 | 55 | 100 | 100 | 100 |
|  | 50 | 100 | 100 | — | 100 | 100 | 100 |
|  | 10 | 99 | 100 | — | 95 | 100 | 100 |
|  | 2 | 80 | 95 | — | 85 | 100 | 100 |
| 48 | 100 | 100 | 100 | 50 | 100 | 100 | 100 |
|  | 50 | 100 | 100 | — | 100 | 100 | 100 |
|  | 10 | 100 | 98 | — | 99 | 100 | 100 |
|  | 2 | 90 | 95 | — | 70 | 100 | 99 |
| 49 | 100 | 100 | 100 | 30 | 100 | 100 | 100 |
|  | 50 | 100 | 100 | — | 100 | 100 | 100 |
|  | 10 | 100 | 98 | — | 99 | 100 | 100 |
|  | 2 | 93 | 95 | — | 97 | 100 | 100 |
| 50 | 100 | 100 | 100 | 20 | 100 | 100 | 100 |
|  | 50 | 100 | 100 | — | 100 | 100 | 100 |
|  | 10 | 98 | 98 | — | 99 | 100 | 100 |
|  | 2 | 85 | 95 | — | 90 | 100 | 100 |
| 51 | 100 | 100 | 100 | 75 | 100 | 100 | 100 |
|  | 50 | 100 | 100 | — | 100 | 100 | 100 |
|  | 10 | 100 | 98 | — | 97 | 100 | 100 |
|  | 2 | 90 | 90 | — | 90 | 100 | 100 |
| 52 | 100 | 100 | 100 | 45 | 100 | 100 | 100 |
|  | 50 | 100 | 100 | — | 100 | 100 | 100 |
|  | 10 | 100 | 100 | — | 100 | 100 | 100 |
|  | 2 | 70 | 95 | — | 95 | 100 | 99 |
| 53 | 100 | 100 | 100 | 50 | 100 | 100 | 100 |
|  | 50 | 100 | 100 | — | 100 | 100 | 100 |
|  | 10 | 97 | 98 | — | 99 | 100 | 100 |
|  | 2 | 70 | 85 | — | 90 | 100 | 100 |
| 54 | 100 | 100 | 100 | 65 | 100 | 100 | 100 |
|  | 50 | 100 | 100 | — | 100 | 100 | 100 |
|  | 10 | 90 | 98 | — | 95 | 100 | 100 |
|  | 2 | 30 | 90 | — | 93 | 100 | 100 |
| 55 | 100 | 100 | 100 | 75 | 100 | 100 | 100 |
|  | 50 | 100 | 100 | 25 | 100 | 100 | 100 |
|  | 10 | 100 | 100 | — | 100 | 100 | 100 |
|  | 2 | 100 | 90 | — | 99 | 100 | 100 |
| 56 | 100 | 100 | 100 | 65 | 100 | 100 | 100 |
|  | 50 | 100 | 100 | 20 | 100 | 100 | 100 |
|  | 10 | 100 | 100 | — | 100 | 100 | 100 |
|  | 2 | 97 | 95 | — | 95 | 100 | 100 |
| 57 | 100 | 100 | 100 | 75 | 100 | 100 | 100 |
|  | 50 | 100 | 100 | 20 | 100 | 100 | 100 |
|  | 10 | 100 | 100 | — | 100 | 100 | 100 |
|  | 2 | 90 | 90 | — | 99 | 95 | 100 |
| 58 | 100 | 100 | 100 | 35 | 100 | 100 | 100 |
|  | 50 | 100 | 100 | — | 100 | 100 | 100 |
|  | 10 | 100 | 100 | — | 100 | 100 | 100 |
|  | 2 | 100 | 90 | — | 99 | 100 | 100 |
| 59 | 100 | 100 | 100 | 65 | 100 | 100 | 100 |
|  | 50 | 100 | 100 | — | 100 | 100 | 100 |
|  | 10 | 100 | 100 | — | 100 | 100 | 100 |
|  | 2 | 97 | 98 | — | 98 | 90 | 98 |
| 60 | 100 | 100 | 100 | 45 | 100 | 100 | 100 |
|  | 50 | 100 | 100 | — | 95 | 100 | 100 |
|  | 10 | 96 | 100 | — | 92 | 100 | 98 |
|  | 2 | 80 | 98 | — | 70 | 95 | 95 |
| 61 | 100 | 100 | 100 | 85 | 100 | 100 | 100 |
|  | 50 | 100 | 100 | 40 | 100 | 100 | 100 |
|  | 10 | 100 | 100 | — | 100 | 100 | 100 |
|  | 2 | 99 | 95 | — | 99 | 100 | 100 |
| 62 | 100 | 100 | 100 | 85 | 100 | 100 | 100 |
|  | 50 | 100 | 100 | 30 | 100 | 100 | 100 |
|  | 10 | 100 | 100 | — | 100 | 100 | 100 |
|  | 2 | 90 | 93 | — | 99 | 100 | 99 |
| 63 | 100 | 100 | 100 | 75 | 100 | 100 | 100 |
|  | 50 | 100 | 100 | 20 | 100 | 100 | 100 |
|  | 10 | 100 | 100 | — | 100 | 100 | 100 |
|  | 2 | 100 | 90 | — | 99 | 100 | 100 |
| 64 | 100 | 100 | 100 | 80 | 100 | 100 | 100 |
|  | 50 | 100 | 100 | 40 | 100 | 100 | 100 |
|  | 10 | 100 | 100 | — | 100 | 100 | 100 |
|  | 2 | 100 | 95 | — | 99 | 100 | 97 |
| 65 | 100 | 100 | 100 | 35 | 100 | 100 | 100 |
|  | 50 | 100 | 100 | — | 100 | 100 | 100 |
|  | 10 | 100 | 100 | — | 80 | 100 | 95 |
|  | 2 | 100 | 97 | — | 50 | 100 | 60 |
| 66 | 100 | 100 | 100 | 45 | 100 | 100 | 100 |
|  | 50 | 100 | 100 | — | 98 | 100 | 100 |
|  | 10 | 90 | 98 | — | 90 | 100 | 100 |
|  | 2 | 60 | 65 | — | 75 | 95 | 97 |
| 67 | 100 | 100 | 100 | 85 | 100 | 100 | 100 |
|  | 50 | 100 | 100 | 40 | 100 | 100 | 100 |
|  | 10 | 100 | 100 | — | 100 | 100 | 100 |
|  | 2 | 100 | 100 | — | 99 | 100 | 100 |
| 68 | 100 | 100 | 100 | 70 | 100 | 100 | 100 |
|  | 50 | 100 | 100 | 20 | 100 | 100 | 100 |
|  | 10 | 100 | 100 | — | 100 | 100 | 100 |
|  | 2 | 100 | 100 | — | 100 | 100 | 100 |

TABLE 4-continued

| Comp. No. | Conc. (ppm) | RCB | RSB | CGM | TLB | WLR | BPM |
|---|---|---|---|---|---|---|---|
| 69 | 100 | 100 | 100 | 60 | 100 | 100 | 100 |
|  | 50 | 100 | 100 | — | 100 | 100 | 100 |
|  | 10 | 100 | 100 | — | 100 | 100 | 100 |
|  | 2 | 100 | 100 | — | 100 | 100 | 100 |
| 70 | 100 | 100 | 100 | 50 | 100 | 100 | 100 |
|  | 50 | 100 | 100 | — | 90 | 100 | 100 |
|  | 10 | 100 | 100 | — | 35 | 100 | 100 |
|  | 2 | 100 | 100 | — | — | 100 | 100 |
| 71 | 100 | 100 | 100 | 65 | 100 | 100 | 100 |
|  | 50 | 100 | 100 | — | 98 | 100 | 100 |
|  | 10 | 90 | 98 | — | 90 | 100 | 100 |
|  | 2 | 30 | 65 | — | 70 | 95 | 95 |
| 72 | 100 | 100 | 100 | 79 | 100 | 100 | 100 |
|  | 50 | 100 | 100 | — | 100 | 100 | 100 |
|  | 10 | 99 | 98 | — | 90 | 100 | 100 |
|  | 2 | 80 | 75 | — | 70 | 97 | 98 |
| 73 | 100 | 100 | 10 | 20 | 100 | 100 | 95 |
|  | 50 | 100 | — | — | 90 | 100 | 93 |
|  | 10 | 90 | — | — | 10 | 100 | 60 |
|  | 2 | 70 | — | — | — | 100 | 15 |
| 74 | 100 | 100 | 100 | 35 | 100 | 100 | 100 |
|  | 50 | 100 | 90 | — | 90 | 100 | 100 |
|  | 10 | 90 | 80 | — | 80 | 99 | 100 |
|  | 2 | 10 | 67 | — | — | 90 | 92 |
| 75 | 100 | 100 | 100 | 40 | 100 | 100 | 100 |
|  | 50 | 100 | 100 | — | 98 | 100 | 100 |
|  | 10 | 90 | 98 | — | 90 | 100 | 98 |
|  | 2 | 30 | 65 | — | 70 | 95 | 92 |
| 76 | 100 | 100 | 100 | 45 | 100 | 100 | 100 |
|  | 50 | 100 | 100 | — | 98 | 100 | 100 |
|  | 10 | 90 | 98 | — | 90 | 100 | 100 |
|  | 2 | 30 | 65 | — | 70 | 95 | 95 |
| 77 | 100 | 100 | 100 | 70 | 100 | 100 | 100 |
|  | 50 | 100 | 100 | — | 98 | 100 | 100 |
|  | 10 | 90 | 98 | — | 90 | 100 | 100 |
|  | 2 | 30 | 65 | — | 70 | 95 | 90 |
| 78 | 100 | 100 | 100 | 40 | 100 | 100 | 100 |
|  | 50 | 98 | 100 | — | 98 | 100 | 100 |
|  | 10 | 90 | 98 | — | 90 | 98 | 100 |
|  | 2 | 40 | 65 | — | 70 | 95 | 90 |
| 79 | 100 | 100 | 100 | 40 | 100 | 100 | 100 |
|  | 50 | 100 | 100 | — | 98 | 100 | 100 |
|  | 10 | 98 | 98 | — | 90 | 100 | 100 |
|  | 2 | 80 | 85 | — | 70 | 95 | 90 |
| 80 | 100 | 100 | 100 | 55 | 100 | 100 | 100 |
|  | 50 | 100 | 100 | — | 98 | 100 | 100 |
|  | 10 | 90 | 98 | — | 90 | 100 | 100 |
|  | 2 | 35 | 65 | — | 70 | 95 | 90 |
| 81 | 100 | 100 | 100 | 60 | 100 | 100 | 100 |
|  | 50 | 100 | 100 | — | 98 | 100 | 100 |
|  | 10 | 90 | 98 | — | 90 | 100 | 100 |
|  | 2 | 70 | 55 | — | 60 | 95 | 98 |
| 82 | 100 | 100 | 100 | 0 | 90 | 100 | 95 |
|  | 50 | 100 | 99 | — | 90 | 100 | 95 |
|  | 10 | 90 | 90 | — | 30 | 100 | 90 |
|  | 2 | 70 | 70 | — | — | 98 | 5 |
| 83 | 100 | 100 | 100 | 50 | 100 | 100 | 100 |
|  | 50 | 100 | 100 | — | 98 | 100 | 100 |
|  | 10 | 90 | 98 | — | 90 | 100 | 100 |
|  | 2 | 50 | 75 | — | 70 | 95 | 95 |
| 84 | 100 | 100 | 100 | 70 | 100 | 100 | 100 |
|  | 50 | 100 | 100 | — | 98 | 100 | 100 |
|  | 10 | 90 | 98 | — | 90 | 100 | 100 |
|  | 2 | 30 | 55 | — | 70 | 95 | 90 |
| 85 | 100 | 100 | 99 | 35 | 100 | 100 | 100 |
|  | 50 | 100 | 96 | — | 100 | 100 | 97 |
|  | 10 | 90 | 85 | — | 20 | 99 | 70 |
|  | 2 | 70 | 60 | — | — | 80 | 25 |
| 86 | 100 | 100 | 100 | 40 | 100 | 100 | 100 |
|  | 50 | 100 | 100 | — | 98 | 100 | 100 |
|  | 10 | 90 | 98 | — | 90 | 100 | 100 |
|  | 2 | 30 | 65 | — | 70 | 95 | 90 |
| Azoxystrobin | 50 | 100 | 100 | 40 | 100 | 100 | 100 |
|  | 10 | 100 | 100 | — | 98 | 100 | 100 |
|  | 2 | 90 | 98 | — | 90 | 100 | 100 |
|  | 0.4 | 30 | 67 | — | 50 | 95 | 95 |
| Fenarimol | 50 | 20 | 100 | 30 | 95 | 100 | 100 |
|  | 10 | 0 | 85 | 7 | 80 | 100 | 100 |
|  | 2 | — | 40 | 7 | 75 | 80 | 100 |
|  | 0.4 | — | 30 | 7 | 65 | 15 | 95 |
| Kresoximmethyl | 50 | 100 | 100 | 30 | 100 | 100 | 100 |
|  | 10 | 95 | 98 | — | 95 | 100 | 100 |
|  | 2 | 60 | 90 | — | 80 | 95 | 100 |
|  | 0.4 | 30 | 67 | — | 30 | 85 | 95 |

As shown in Table 4, the compounds of the present invention have a broad fungicidal spectrum against the target fungi when compared with the control compounds such as Azoxystrobin, Fenarimol. and Kresoxim-methyl. In particular, the inventive compounds have excellent fungicidal activity against RCB, RSB, TLB, WLR and BPM even at a concentration of 2 ppm.

INDUSTRIAL APPLICABILITY

The methoxyimino compound of formula (I) of the present invention having a high fungicidal activity against various crops even at a low concentration can be used as a fungicide.

While the invention has been described with respect to the above specific embodiments, it should be recognized that various modifications and changes may be made and also fall within the scope of the invention as defined by the claims that follow.

The invention claimed is:

1. A methoxyimino compound of formula (I):

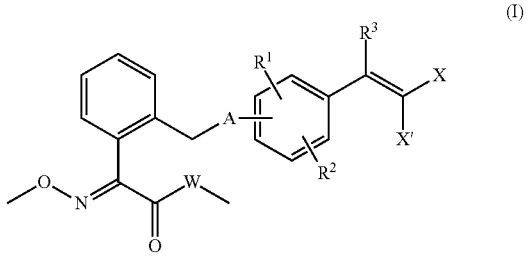

wherein,
A is O or O—N=C(CH$_3$);
R$^1$ is H, halogen, C$_{1-3}$ alkyl, or C$_{1-3}$ alkoxy;
R$^2$ is H or C$_{1-3}$ alkoxy;
R$^3$ is H, or C$_{1-4}$ alkyl substituted with one or more C$_{1-4}$ alkyl groups or halogens;
X and X' are each independently halogen; and
W is O or NH.

2. The methoxyimino compound of claim 1, wherein X and X' are each independently F, Cl or Br; R$^1$ is H, F, Cl, Br, methyl, methoxy or ethoxy; R$^2$ is H or methoxy; and R$^3$ is H, or C$_{1-4}$ alkyl substituted with one or more fluorines.

3. The methoxyimino compound of claim 1, which is selected from the group consisting of:
(1) methyl-(E)-2-(2-((3-(2,2-dichlorovinyl)phenoxy)methyl)phenyl)-2-methoxyiminoacetate;
(2) (E)-2-(2-((3-(2,2-dichlorovinyl)phenoxy)methyl)phenyl)-2-methoxyimino-N-methylacetamide;
(3) methyl-(E)-2-(2-((4-(2,2-dichlorovinyl)phenoxy)methyl)phenyl)-2-methoxyiminoacetate;

(4) (E)-2-(2-((4-(2,2-dichlorovinyl)phenoxy)methyl)phenyl)-2-methoxyimino-N-methylacetamide;
(5) methyl-(E)-2-(2-((3-(2,2-dibromovinyl)phenoxy)methyl)phenyl)-2-methoxyiminoacetate;
(6) (E)-2-(2-((3-(2,2-dibromovinyl)phenoxy)methyl)phenyl)-2-methoxyimino-N-methylacetamide;
(7) methyl-(E)-2-(2-((4-(2,2-dibromovinyl)phenoxy)methyl)phenyl)-2-methoxyiminoacetate;
(8) (E)-2-(2-((4-(2,2-dibromovinyl)phenoxy)methyl)phenyl)-2-methoxyimino-N-methylacetamide;
(9) methyl-(E)-2-(2-((4-(2,2-difluorovinyl)phenoxy)methyl)phenyl)-2-methoxyiminoacetate;
(10) (E)-2-(2-((4-(2,2-difluorovinyl)phenoxy)methyl)phenyl)-2-methoxyimino-N-methylacetamide;
(11) methyl-(2E)-2-(2-((3-(2-chloro-2-fluorovinyl)phenoxy))methyl)phenyl)-2-methoxyiminoacetate;
(12) (2E)-2-(2-((3-(2-chloro-2-difluorovinyl)phenoxy)methyl)phenyl)-2-methoxyimino-N-methylacetamide;
(13) methyl-(2E)-2-(2-((4-(2-chloro-2-fluorovinyl)phenoxy)methyl)phenyl)-2-methoxyiminoacetate;
(14) (2E)-2-(2-((4-(2-chloro-2-difluorovinyl)phenoxy)methyl)phenyl)-2-methoxyimino-N-methylacetamide;
(15) methyl-(2E)-2-(2-((3-(2-bromo-2-chlorovinyl)phenoxy)methyl)phenyl)-2-methoxyiminoacetate;
(16) (2E)-2-(2-((3-(2-bromo-2-chlorovinyl)phenoxy)methyl)phenyl)-2-methoxyimino-N-methylacetamide;
(17) methyl-(2E)-2-(2-((4-(2-bromo-2-chlorovinyl)phenoxy)methyl)phenyl)-2-methoxyiminoacetate;
(18) (2E)-2-(2-((4-(2-bromo-2-chlorovinyl)phenoxy)methyl)phenyl)-2-methoxyimino-N-methylacetamide;
(19) methyl-(E)-2-[[[[[2-[3-(2,2-dichlorovinyl)phenyl](1-methyl)methylidene]amino]oxy]methyl]phenyl]-2-methoxyiminoacetate;
(20) (E)-2-[[[[[2-[3-(2,2-dichlorovinyl)phenyl](1-methyl)methylidene]amino]oxy]methyl]phenyl]-2-methoxyimino-N-methylacetamide;
(21) methyl-(E)-2-[[[[[2-[4-(2,2-dichlorovinyl)phenyl](1-methyl)methylidene]amino]oxy]methyl]phenyl]-2-methoxyiminoacetate;
(22) (E)-2-[[[[[2-[4-(2,2-dichlorovinyl)phenyl](1-methyl)methylidene]amino]oxy]methyl]phenyl]-2-methoxyimino-N-methylacetamide;
(23) methyl-(E)-2-[[[[[2-[3-(2,2-dibromovinyl)phenyl](1-methyl)methylidene]amino]oxy]methyl]phenyl]-2-methoxyiminoacetate;
(24) (E)-2-[[[[[2-[3-(2,2-dibromovinyl)phenyl](1-methyl)methylidene]amino]oxy]methyl]phenyl]-2-methoxyimino-N-methylacetamide;
(25) methyl-(E)-2-[[[[[2-[4-(2,2-dibromovinyl)phenyl](1-methyl)methylidene]amino]oxy]methyl]phenyl]-2-methoxyiminoacetate;
(26) (E)-2-[[[[[2-[4-(2,2-dibromovinyl)phenyl](1-methyl)methylidene]amino]oxy]methyl]phenyl]-2-methoxyimino-N-methylacetamide;
(27) methyl-(E)-2-[[[[[2-[3-(2,2-difluorovinyl)phenyl](1-methyl)methylidene]amino]oxy]methyl]phenyl]-2-methoxyiminoacetate;
(28) (E)-2-[[[[[2-[3-(2,2-difluorovinyl)phenyl](1-methyl)methylidene]amino]oxy]methyl]phenyl]-2-methoxyimino-N-methylacetamide;
(29) methyl-(E)-2-[[[[[2-[4-(2,2-difluorovinyl)phenyl](1-methyl)methylidene]amino]oxy]methyl]phenyl]-2-methoxyiminoacetate;
(30) (E)-2-[[[[[2-[4-(2,2-difluorovinyl)phenyl](1-methyl)methylidene]amino]oxy]methyl]phenyl]-2-methoxyimino-N-methylacetamide;
(31) methyl-(E)-2-[[[[[2-[3-(2-chloro-2-fluorovinyl)phenyl](1-methyl)methylidene]amino]oxy]methyl]phenyl]-2-methoxyiminoacetate;
(32) (E)-2-[[[[[2-[3-(2-chloro-2-fluorovinyl)phenyl](1-methyl)methylidene]amino]oxy]methyl]phenyl]-2-methoxyimino-N-methylacetamide;
(33) methyl-(E)-2-[[[[[2-[4-(2-chloro-2-fluorovinyl)phenyl](1-methyl)methylidene]amino]oxy]methyl]phenyl]-2-methoxyiminoacetate;
(34) (E)-2-[[[[[2-[4-(2-chloro-2-fluorovinyl)phenyl](1-methyl)methylidene]amino]oxy]methyl]phenyl]-2-methoxyimino-N-methylacetamide;
(35) methyl-(E)-2-[[[[[2-[3-(2-bromo-2-chlorovinyl)phenyl](1-methyl)methylidene]amino]oxy]methyl]phenyl]-2-methoxyiminoacetate;
(36) (E)-2-[[[[[2-[3-(2-bromo-2-chlorovinyl)phenyl](1-methyl)methylidene]amino]oxy]methyl]phenyl]-2-methoxyimino-N-methylacetamide;
(37) methyl-(E)-2-[[[[[2-[4-(2-bromo-2-chlorovinyl)phenyl](1-methyl)methylidene]amino]oxy]methyl]phenyl]-2-methoxyiminoacetate;
(38) (E)-2-[[[[[2-[4-(2-bromo-2-chlorovinyl)phenyl](1-methyl)methylidene]amino]oxy]methyl]phenyl]-2-methoxyimino-N-methylacetamide;
(39) methyl-(E)-2-(2-((2-chloro-4-(2,2-dichlorovinyl)phenoxy)methyl)phenyl)-2-methoxyiminoacetate;
(40) (E)-2-(2-((2-chloro-4-(2,2-dichlorovinyl)phenoxy)methyl)phenyl)-2-methoxyimino-N-methylacetamide;
(41) methyl-(E)-2-(2-((4-(2,2-dichlorovinyl)-2-methylphenoxy)methyl)phenyl)-2-methoxyiminoacetate;
(42) (E)-2-(2-((4-(2,2-dichlorovinyl)-2-methylphenoxy)methyl)phenyl)-2-methoxyimino-N-methylacetamide;
(43) methyl-(E)-2-(2-((2-chloro-3-(2,2-dichlorovinyl)phenoxy)methyl)phenyl)-2-methoxyiminoacetate;
(44) (E)-2-(2-((2-chloro-3-(2,2-dichlorovinyl)phenoxy)methyl)phenyl)-2-methoxyimino-N-methylacetamide;
(45) methyl-(E)-2-(2-((2-(2,2-dichlorovinyl)-4-methylphenoxy)methyl)phenyl)-2-methoxyiminoacetate;
(46) (E)-2-(2-((2-(2,2-dichlorovinyl)-4-methylphenoxy)methyl)phenyl)-2-methoxyimino-N-methylacetamide;
(47) methyl-(E)-2-(2-((5-(2,2-dichlorovinyl)-2-methoxyphenoxy)methyl)phenyl)-2-methoxyiminoacetate;
(48) (E)-2-(2-((5-(2,2-dichlorovinyl)-2-methoxyphenoxy)methyl)phenyl)-2-methoxyimino-N-methylacetamide;
(49) methyl-(E)-2-(2-((2-(2,2-dichlorovinyl)-6-methylphenoxy)methyl)phenyl)-2-methoxyiminoacetate;
(50) (E)-2-(2-((2-(2,2-dichlorovinyl)-6-methylphenoxy)methyl)phenyl)-2-methoxyimino-N-methylacetamide;
(51) methyl-(E)-2-(2-((2-bromo-3-(2,2-dichlorovinyl)-6-methoxyphenoxy)methyl)phenyl)-2-methoxyiminoacetate;
(52) (E)-2-(2-((2-(2-bromo-3-(2,2-dichlorovinyl)-6-phenoxy)methyl)phenyl)-2-methoxyimino-N-methylacetamide;
(53) methyl-(E)-2-(2-((2-bromo-4-(2,2-dichlorovinyl)phenoxy)methyl)phenyl)-2-methoxyiminoacetate;
(54) (E)-2-(2-((2-bromo-4-(2,2-dichlorovinyl)phenoxy)methyl)phenyl)-2-methoxyimino-N-methylacetamide;
(55) methyl-(E)-2-(2-((2-(2,2-dichlorovinyl)-4-fluorophenoxy)methyl)phenyl)-2-methoxyiminoacetate;
(56) (E)-2-(2-((2-(2,2-dichlorovinyl)-4-fluorophenoxy)methyl)phenyl)-2-methoxyimino-N-methylacetamide;
(57) methyl-(E)-2-(2-((3-chloro-4-(2,2-dichlorovinyl)phenoxy)methyl)phenyl)-2-methoxyiminoacetate;
(58) (E)-2-(2-((3-chloro-4-(2,2-dichlorovinyl)phenoxy)methyl)phenyl)-2-methoxyimino-N-methylacetamide;

(59) methyl-(E)-2-(2-((4-(2,2-dichlorovinyl)-2-ethoxyphenoxy)methyl)phenyl)-2-methoxyiminoacetate;
(60) (E)-2-(2-((4-(2,2-dichlorovinyl)-2-ethoxyphenoxy)methyl)phenyl)-2-methoxyimino-N-methylacetamide;
(61) methyl-(E)-2-(2-((5-bromo-2-(2,2-dichlorovinyl)phenoxy)methyl)phenyl)-2-methoxyiminoacetate;
(62) (E)-2-(2-((5-bromo-2-(2,2-dichlorovinyl)phenoxy)methyl)phenyl)-2-methoxyimino-N-methylacetamide;
(63) methyl-(E)-2-(2-((4-(2,2-dibromovinyl)-2-chlorophenoxy)methyl)phenyl)-2-methoxyiminoacetate;
(64) (E)-2-(2-((4-(2,2-dibromovinyl)-2-chlorophenoxy)methyl)phenyl)-2-methoxyimino-N-methylacetamide;
(65) methyl-(E)-2-(2-((4-(2,2-dibromovinyl)-2-methylphenoxy)methyl)phenyl)-2-methoxyiminoacetate;
(66) (E)-2-(2-((4-(2,2-dibromovinyl)-2-methylphenoxy)methyl)phenyl)-2-methoxyimino-N-methylacetamide;
(67) methyl-(E)-2-(2-((3-(2,2-dibromovinyl)-2-chlorophenoxy)methyl)phenyl)-2-methoxyiminoacetate;
(68) (E)-2-(2-((3-(2,2-dibromovinyl)-2-chlorophenoxy)methyl)phenyl)-2-methoxyimino-N-methylacetamide;
(69) methyl-(E)-2-(2-((2-(2,2-dibromovinyl)-4-methylphenoxy)methyl)phenyl)-2-methoxyiminoacetate;
(70) (E)-2-(2-((2-(2,2-dibromovinyl)-4-methylphenoxy)methyl)phenyl)-2-methoxyimino-N-methylacetamide;
(71) methyl-(E)-2-(2-((5-(2,2-dibromovinyl)-2-methoxyphenoxy)methyl)phenyl)-2-methoxyiminoacetate;
(72) (E)-2-(2-((5-(2,2-dibromovinyl)-2-methoxyphenoxy)methyl)phenyl)-2-methoxyimino-N-methylacetamide;
(73) methyl-(E)-2-(2-((2-(2,2-dibromovinyl)-6-methylphenoxy)methyl)phenyl)-2-methoxyiminoacetate;
(74) (E)-2-(2-((2-(2,2-dibromovinyl)-6-methylphenoxy)methyl)phenyl)-2-methoxyimino-N-methylacetamide;
(75) methyl-(E)-2-(2-((2-bromo-3-(2,2-dibromovinyl)-6-methoxyphenoxy)methyl)phenyl)-2-methoxyiminoacetate;
(76) (E)-2-(2-((2-(2-bromo-3-(2,2-dibromovinyl)-6-methoxyphenoxy)methyl)phenyl)-2-methoxyimino-N-methylacetamide;
(77) methyl-(E)-2-(2-((2-bromo-4-(2,2-dibromovinyl)phenoxy)methyl)phenyl)-2-methoxyiminoacetate;
(78) (E)-2-(2-((2-bromo-4-(2,2-dibromovinyl)phenoxy)methyl)phenyl)-2-methoxyimino-N-methylacetamide;
(79) methyl-(E)-2-(2-((2-(2,2-dibromovinyl)-4-fluorophenoxy)methyl)phenyl)-2-methoxyiminoacetate;
(80) (E)-2-(2-((2-(2,2-dibromovinyl)-4-fluorophenoxy)methyl)phenyl)-2-methoxyimino-N-methylacetamide;
(81) methyl-(E)-2-(2-((4-(2,2-dibromovinyl)-3-chlorophenoxy)methyl)phenyl)-2-methoxyiminoacetate;
(82) (E)-2-(2-((4-(2,2-dibromovinyl)-3-chlorophenoxy)methyl)phenyl)-2-methoxyimino-N-methylacetamide;
(83) methyl-(E)-2-(2-((4-(2,2-dibromovinyl)-2-ethoxyphenoxy)methyl)phenyl)-2-methoxyiminoacetate;
(84) (E)-2-(2-((4-(2,2-dibromovinyl)-2-ethoxyphenoxy)methyl)phenyl)-2-methoxyimino-N-methylacetamide;
(85) methyl-(E)-2-(2-((5-bromo-2-(2,2-dibromovinyl)phenoxy)methyl)phenyl)-2-methoxyiminoacetate; and
(86) (E)-2-(2-((5-bromo-2-(2,2-dibromovinyl)phenoxy)methyl)phenyl)-2-methoxyimino-N-methylacetamide.

4. A method for preparing a compound of formula (Ia), which comprises subjecting a compound of formula (II) to a substitution reaction with a compound of formula (III) in the presence of a base to obtain the compound of formula (Ia):

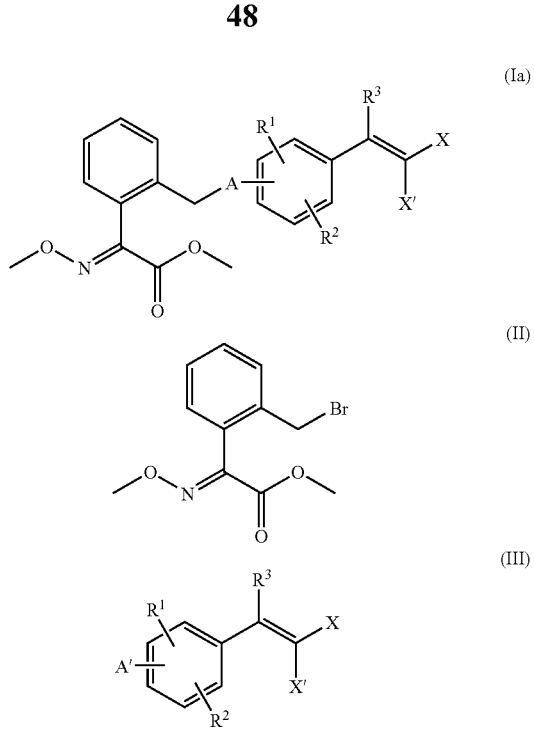

wherein,
A' is OH or $C(CH_3)$=NOH, and
A, X, X', $R^1$, $R^2$ and $R^3$ have the same meanings as defined in claim 1.

5. The method of claim 4, wherein the reaction is carried out at a temperature ranging from $-10°$ C. to $150°$ C.

6. A method for preparing a compound of formula (Ia), which comprises subjecting a compound of formula (IV) to a substitution reaction with a halogenated compound having two or more halogen atoms to obtain the compound of formula (Ia):

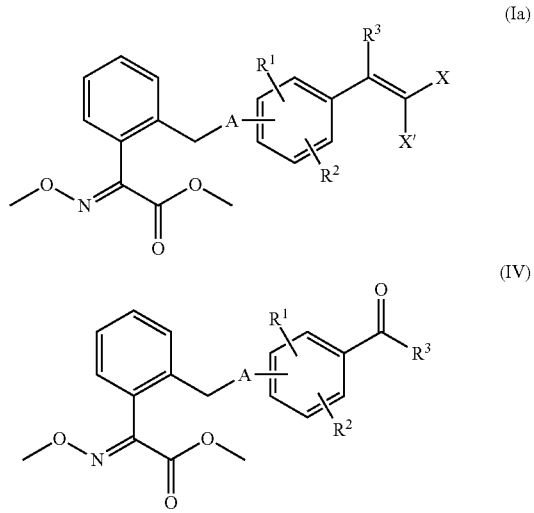

wherein,
A, X, X', $R^1$, $R^2$ and $R^3$ have the same meanings as defined in claim 1.

7. The method of claim 6, wherein the halogenated compound is chloroform, $CCl_4$, $CBr_4$, $CF_2Br_2$, $CFCl_3$, or $CClBr_3$.

8. The method of claim 6, wherein the reaction is carried out at a temperature ranging from 0° C. to 100° C.

9. A method for preparing a compound of formula (Ib), which comprises subjecting a compound of formula (Ia) to amidation to obtain the compound of formula (Ib):

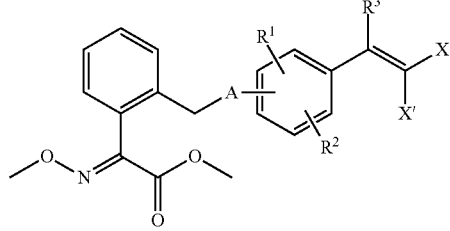
(Ia)

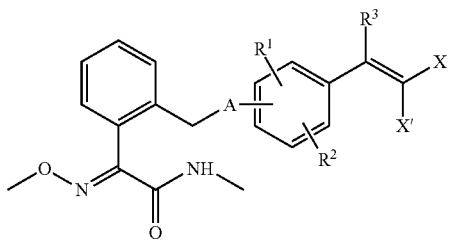
(Ib)

wherein,
A, X, X', $R^1$, $R^2$ and $R^3$ have the same meanings as defined in claim 1.

10. A fungicide composition comprising the methoxy-imino compound of formula (I) of claim 1 as an active ingredient.

* * * * *